(12) United States Patent
Chen et al.

(10) Patent No.: US 8,993,637 B2
(45) Date of Patent: Mar. 31, 2015

(54) USE OF CITRAL FOR TREATING FOCAL SEGMENTAL GLOMERULOSCLEROSIS

(71) Applicant: National Defense Medical Center, Taipei (TW)

(72) Inventors: Ann Chen, Taipei (TW); Kuo-Feng Hua, I-Lan (TW); Shuk-Man Ka, Taipei (TW); Kuo-Ping Chao, Chiayi County (TW); Wen-Liang Chang, Taipei (TW); Kuo-Yuan Hwa, Taipei (TW)

(73) Assignee: National Defense Medical Center, Taipei (TW)

( * ) Notice: Subject to any disclaimer, the term of this patent is extended or adjusted under 35 U.S.C. 154(b) by 0 days.

(21) Appl. No.: 14/251,426

(22) Filed: Apr. 11, 2014

(65) Prior Publication Data
US 2014/0343167 A1 Nov. 20, 2014

(30) Foreign Application Priority Data
Apr. 12, 2013 (TW) .............................. 102113187 A

(51) Int. Cl.
*A61K 31/11* (2006.01)
*A61K 45/06* (2006.01)

(52) U.S. Cl.
CPC ................. *A61K 31/11* (2013.01); *A61K 45/06* (2013.01)
USPC .......................................................... 514/703

(58) Field of Classification Search
CPC .............................. A61K 31/11; A61K 45/06
USPC .......................................................... 514/703
See application file for complete search history.

(56) References Cited

U.S. PATENT DOCUMENTS

| 2,987,551 | A | * | 6/1961 | Baxter et al. | 568/486 |
| 4,409,245 | A | * | 10/1983 | Wolf et al. | 426/9 |
| 6,407,071 | B1 | * | 6/2002 | Rubin | 514/23 |
| 2003/0119715 | A1 | * | 6/2003 | Ward et al. | 514/1 |
| 2006/0241130 | A1 | * | 10/2006 | Keinan et al. | 514/263.31 |
| 2008/0113042 | A1 | * | 5/2008 | Chu et al. | 424/725 |

* cited by examiner

*Primary Examiner* — Raymond Henley, III
(74) *Attorney, Agent, or Firm* — WPAT, P.C.; Anthony King

(57) ABSTRACT

The present invention relates to a new use of citral for manufacturing a medicament for treating focal segmental glomerulosclerosis (FSGS). Particularly, the present invention discloses that citral is effective in alleviating symptoms of FSGS, including reducing glomerular epithelial hyperplasia lesions (EPHLs), peri-glomerular inflammation or glomerular hyalinosis or sclerosis, and also reducing proteinuria or hematuria or lowering serum urea nitrogen level or serum creatinine level in the subject.

5 Claims, 18 Drawing Sheets

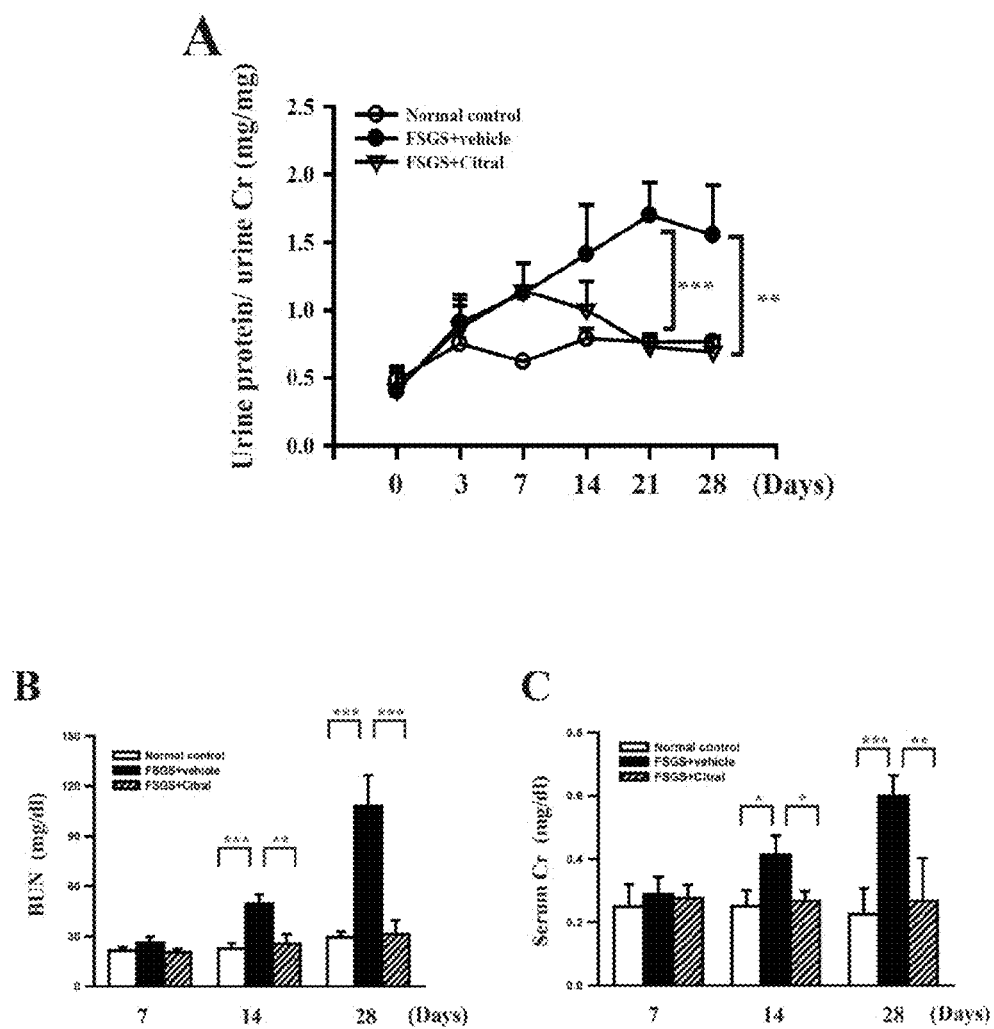
Fig. 1 (Cont')

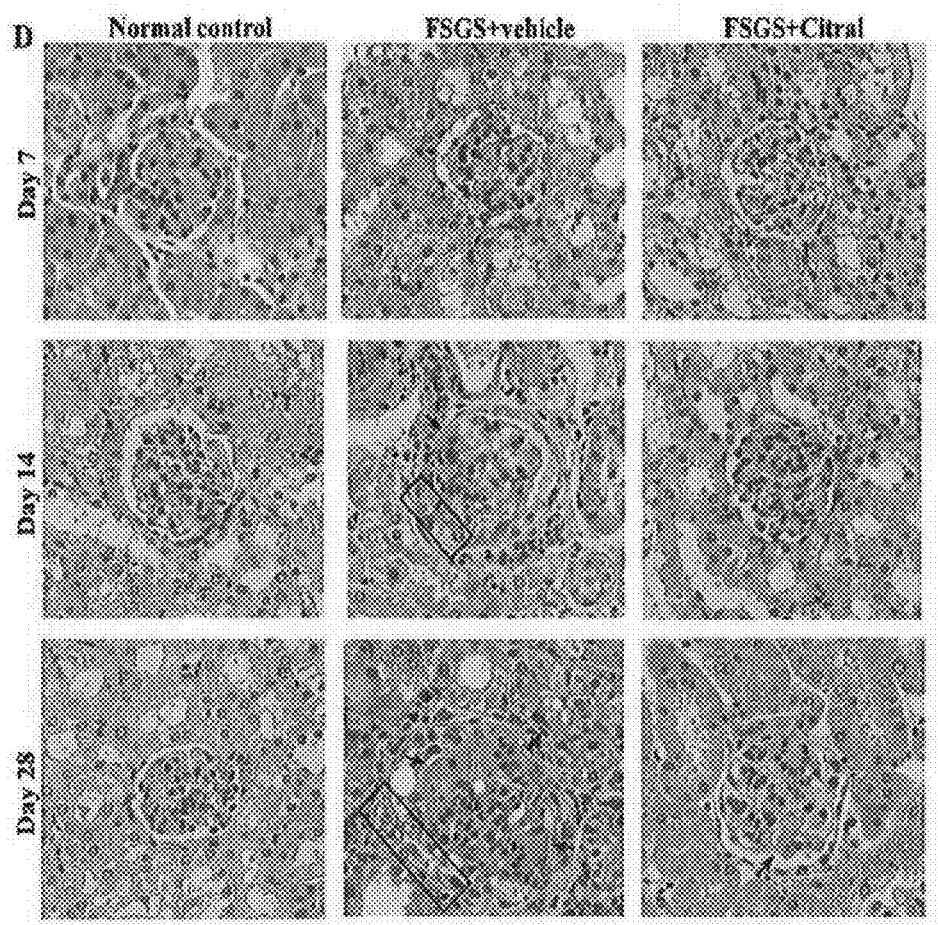
Fig. 1 (Cont')

E
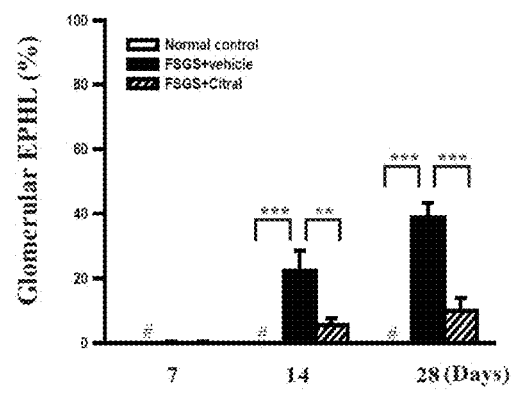
F
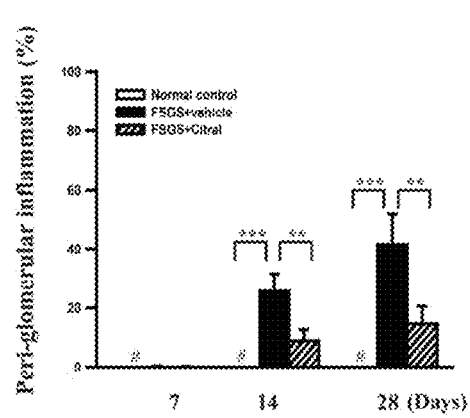
G
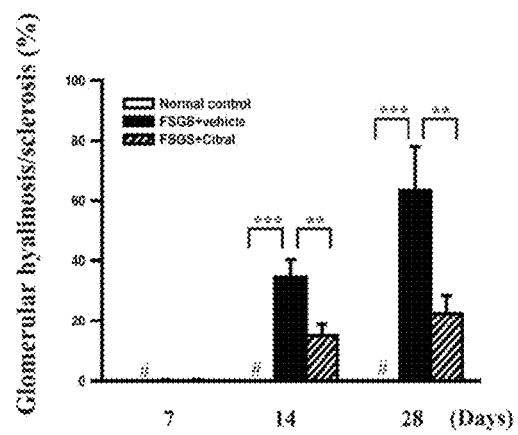
Fig. 1 (Cont')

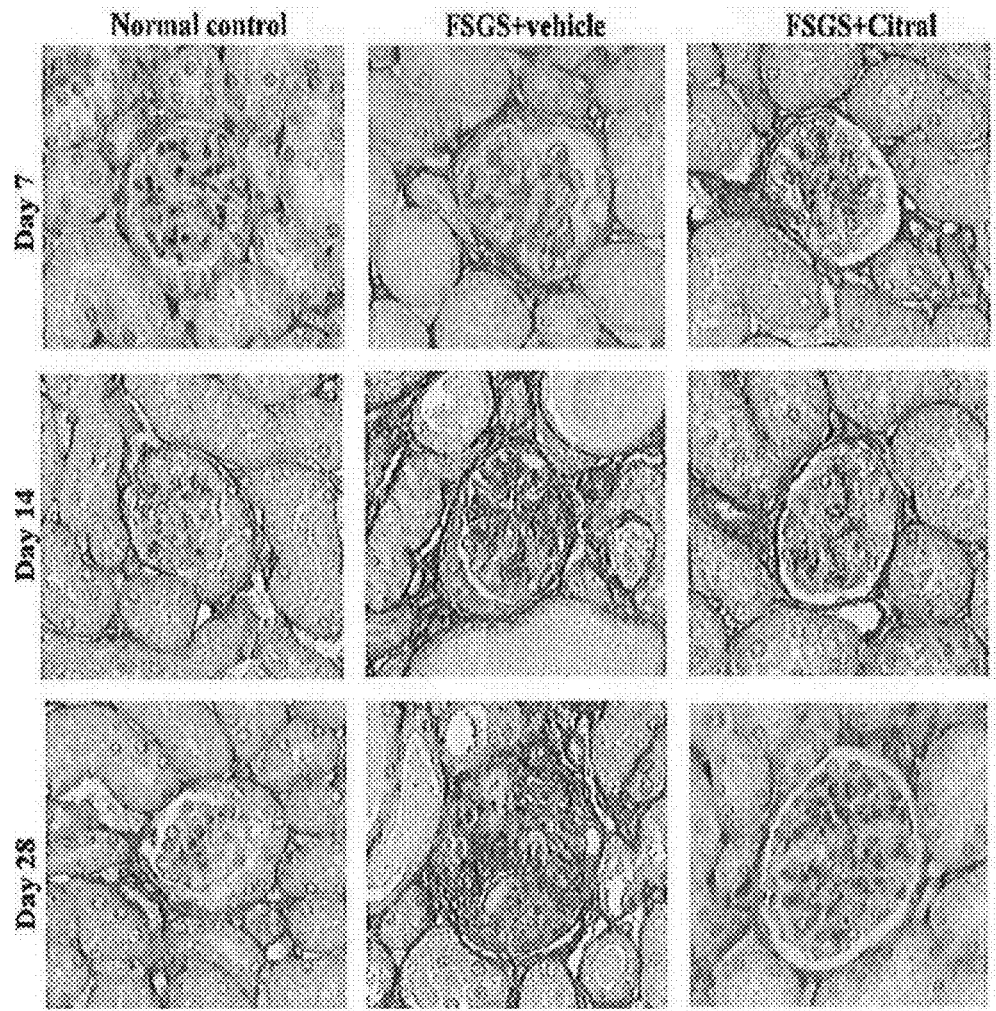
Fig. 1 (Cont')

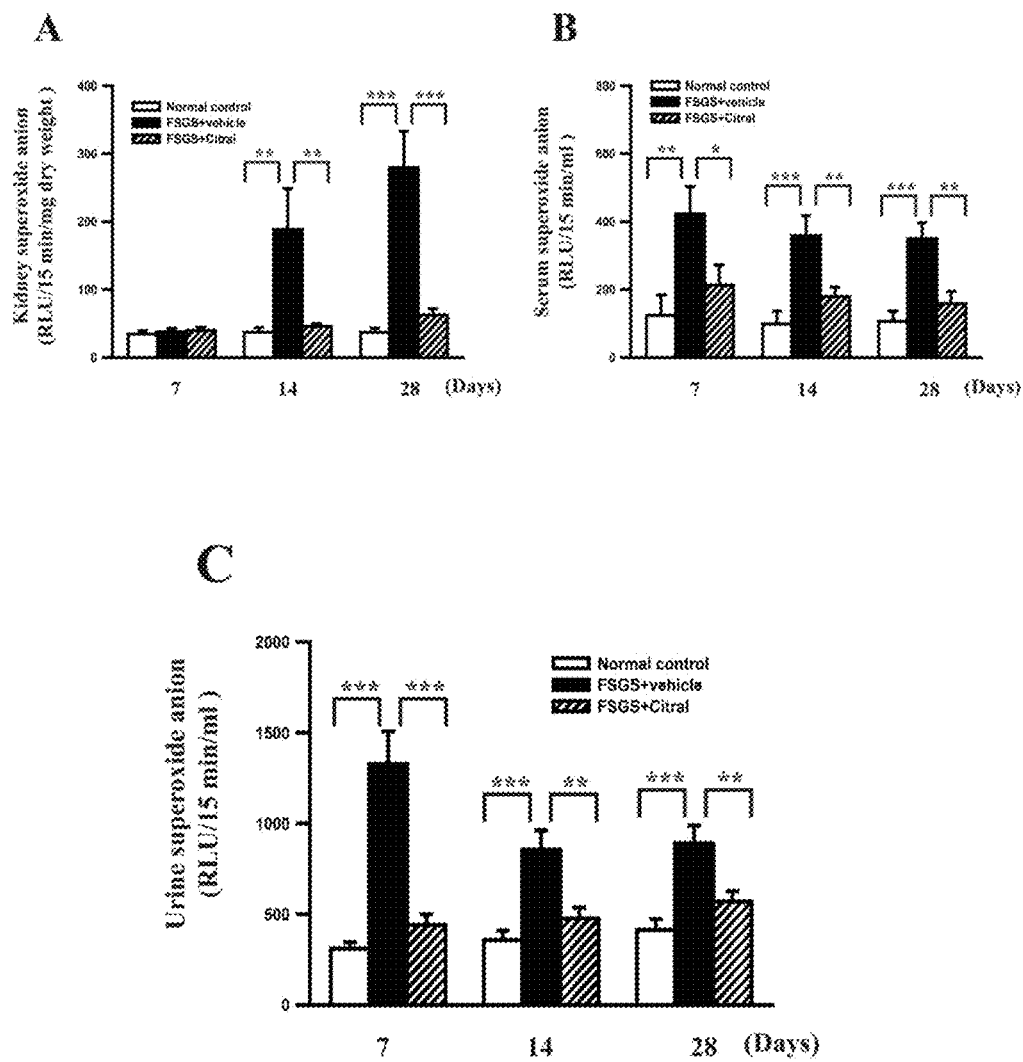
Fig. 2 (Cont')

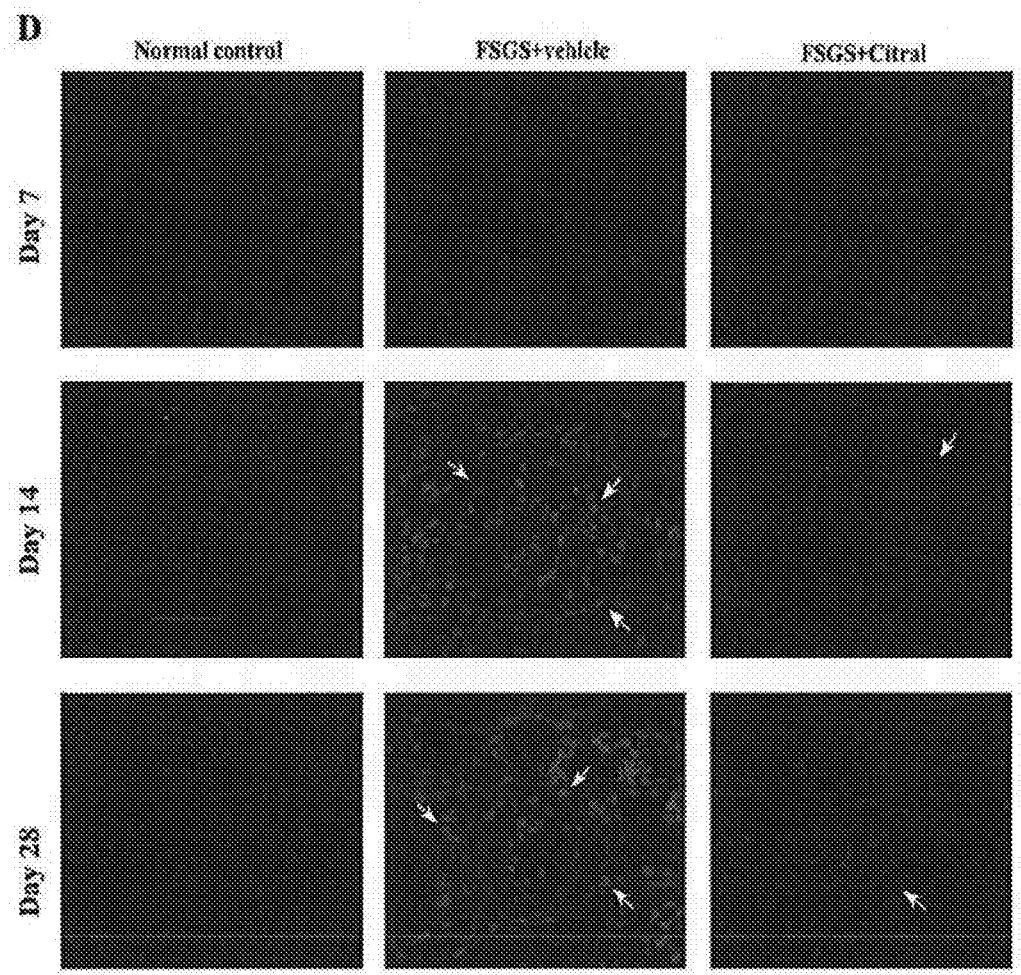
Fig. 2 (Cont')

E

F

G

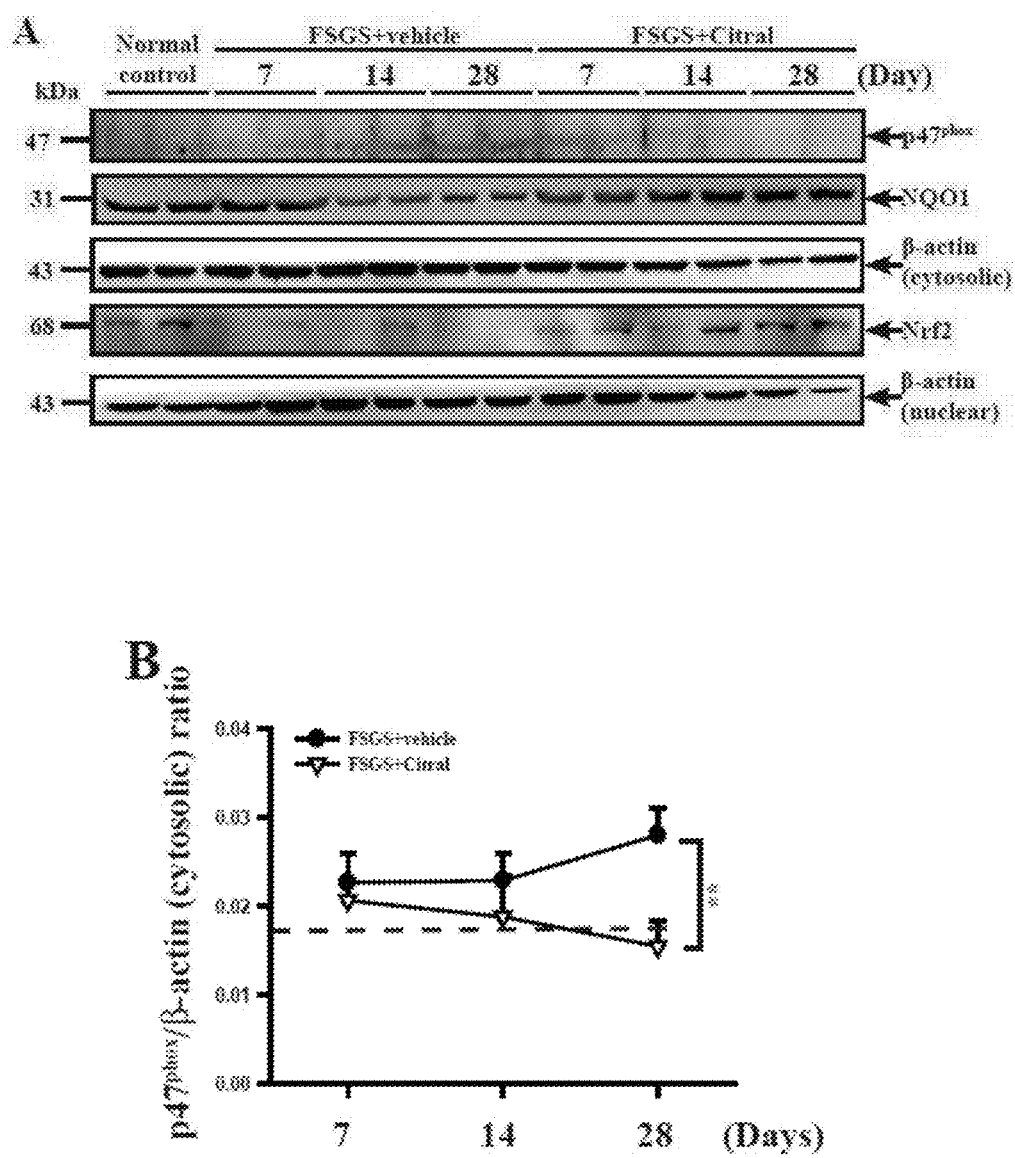
Fig. 3(Cont')

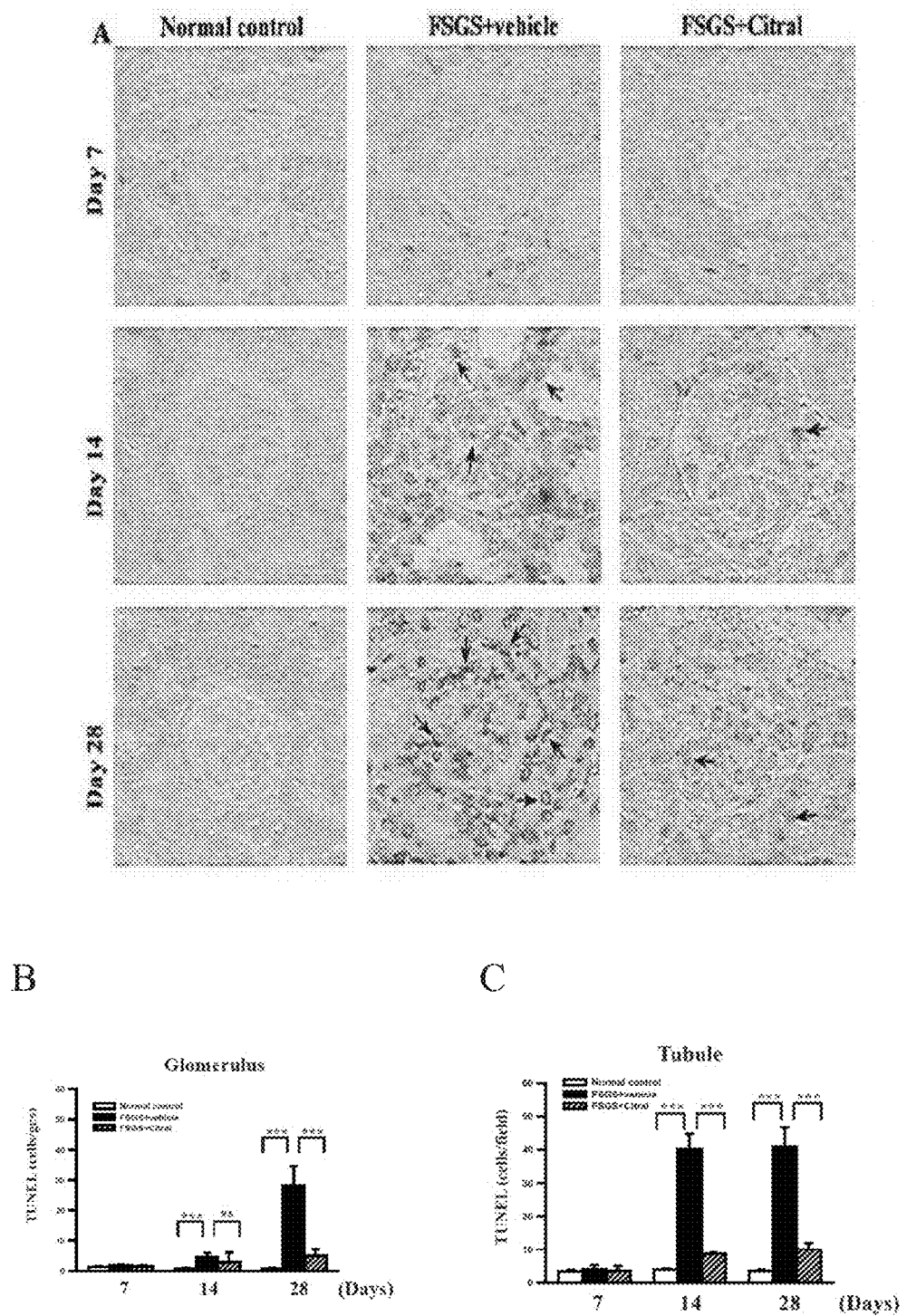
Fig. 4 (Cont')

D

E  F

G

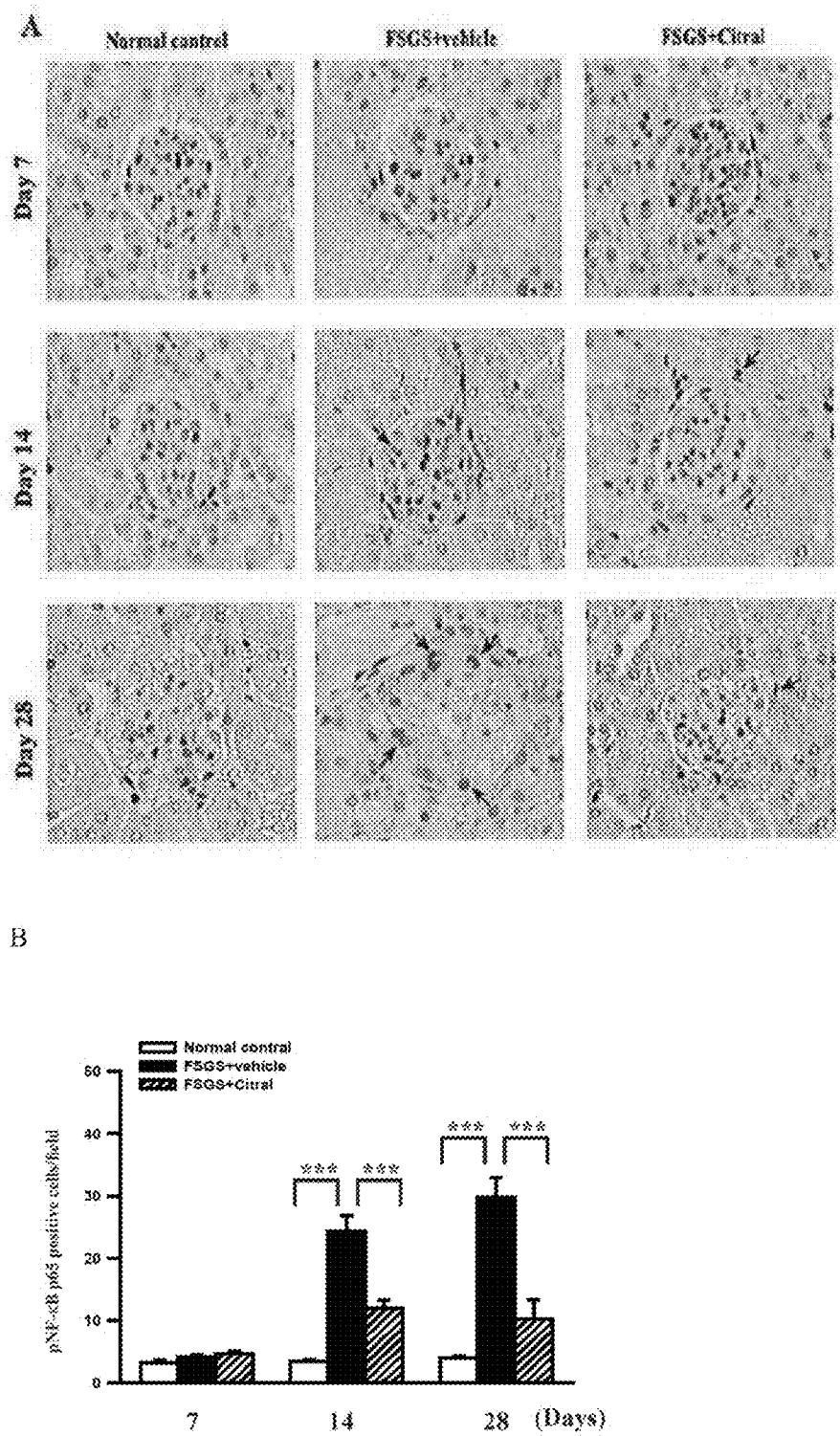
Fig. 5 (Cont')

C

D

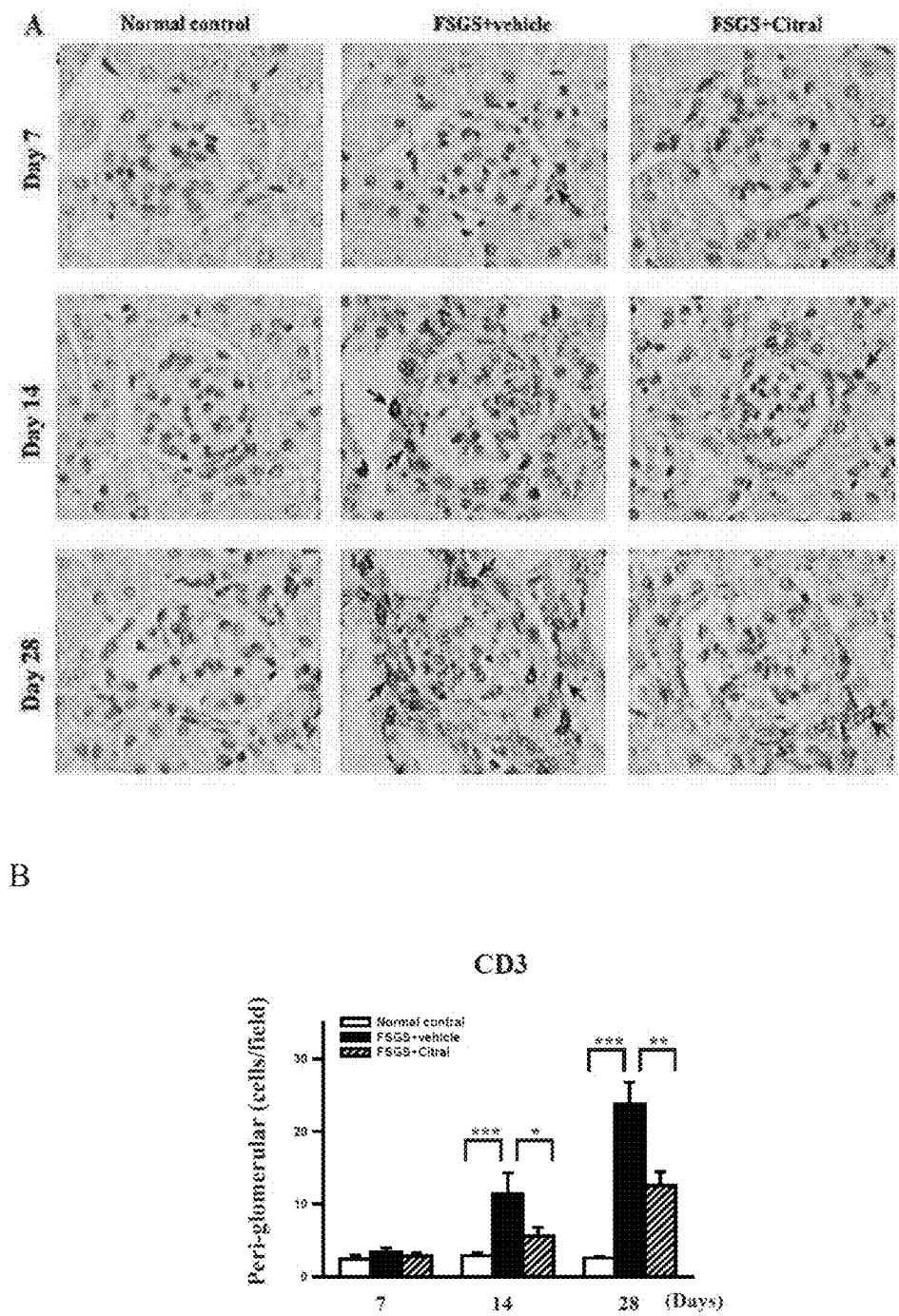
Fig. 6 (Cont')

C

D

USE OF CITRAL FOR TREATING FOCAL SEGMENTAL GLOMERULOSCLEROSIS

RELATED APPLICATIONS

This application claims the benefit of Taiwan Patent Application No. 102113187, filed on Apr. 12, 2013, the entire content of which is incorporated herein by reference.

TECHNOLOGY FIELD

The present invention relates to use of citral for treating focal segmental glomerulosclerosis.

BACKGROUND OF THE INVENTION

Focal segmental glomerulosclerosis (FSGS) manifests with heavy proteinuria in association with focal, but progressive, glomerular sclerosis in the kidney [1-3]. The frequency of end-stage renal disease in patients with FSGS was found to be as high as 78% in long-term follow-up studies [4,5]. Although corticosteroids and other immunomodulatory agents are commonly used to treat these patients [6,7], they result in an unsatisfactory outcome in terms of progression of renal inflammation and fibrosis [8,9] and have various side-effects [10,11]. In addition, the administration of such agents is mostly based on empirical decisions, rather than on targeting specific pathogenic pathways [12]. The establishment of a pathogenesis-based therapeutic strategy is therefore clinically significant.

Citral, that is, 3,7-dimethyl-2,6-octadienal, is an unsaturated chain aldehyde monoterpene containing two double bonds. There are two isomers of citral, with the following structures:

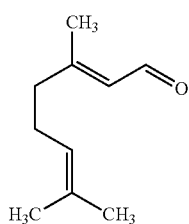

Citral A (E isomer, also known as geranial)

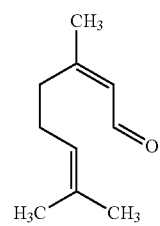

Citral B (Z isomer, also known as neral)

Normally, citral is a mixture of the above two isomers and can be obtained by extraction from citrus plants. It is an oil-like, volatile pale yellow liquid with a lemon scent. Due to its strong lemon scent and taste, citral has been extensively utilized in the cosmetic industry, for example, in perfumes; it has also been used as a safe food additive, for example, in spices. Current studies also showed that citral has anti-bacterial activity, anti-fungal activity and resistance to the genotoxicity induced by the anti-cancer drug bleomycin (see Karabörklü S et al., *Journal of economic entomology*. 104(4): 1212-9, 2011; Molkary Andrea Lôpez et al., *Genetics and Molecular Biology*. 34(3): 479-488, 2011; Singh S A et al., *Natural Product Communications*. 6(9):1221-4, 2011; or Zore G B et al., *Phytomedicine*. 18(13):1181-90, 2011). However, no prior art references has disclosed the use of citral in the treatment of focal segmental glomerulosclerosis.

BRIEF SUMMARY OF THE INVENTION

The present invention is based on the unexpected finding that citral is effective in alleviating the symptoms of focal segmental glomerulosclerosis (FSGS). Therefore, the present invention provides a new approach for treatment of focal segmental glomerulosclerosis (FSGS) in a subject.

In particular, the present invention provides a method for treating focal segmental glomerulosclerosis (FSGS) in a subject in need thereof, which comprises administering a therapeutically effective amount of citral to the subject.

Specifically, the method for treating of the present invention is effective to reduce one or more symptoms of FSGS in the subject selected from the group consisting of glomerular epithelial hyperplasia lesions (EPHLs), peri-glomerular inflammation and glomerular hyalinosis or sclerosis. Also, the method for treating of the present invention is effective to reduce proteinuria or hematuria or lower serum urea nitrogen level or serum creatinine level in the subject.

In some embodiments, citral is orally administered.

In some embodiments, the citral is administered in combination with one or more therapeutic agent for treating focal segmental glomerulosclerosis known in the art, including but not limited to orticosteroid drugs, non-steriodal anti-inflammatory drugs (NSAIDs), immunosuppressants, cytotoxic drugs and vasodilators.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

For the purpose of illustrating the invention, there are shown in the drawings embodiments which are presently preferred. It should be understood, however, that the invention is not limited to the illustrated preferred embodiments. In the drawings.

DETAILED DESCRIPTION OF THE INVENTION

Figure 1:
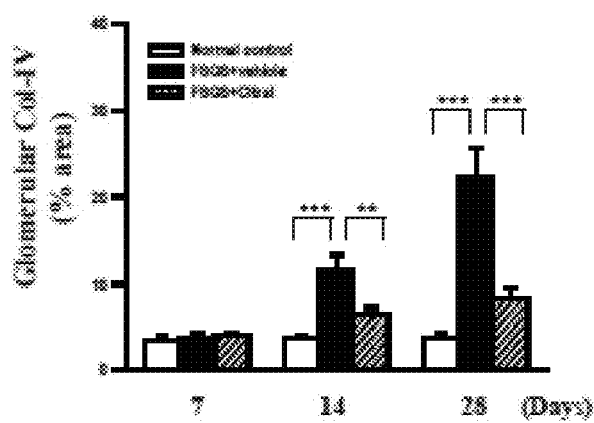
FIG. 1 shows urine protein, renal function, renal histopathology, and hyalinosis/sclerosis. (A) Urine protein time-course study. (B) Serum BUN levels on days 7, 14, and 28. (C) Serum creatinine levels on days 7, 14, and 28. (D) Kidney histopathological evaluation by H&E staining on days 7, 14, and 28. The arrows indicate hyalinosis/sclerosis, and the rectangles EPHLs. (H) Immunohistochemical staining for renal Col-IV. In (D) and (H), the original magnification was 400× and the scoring is shown in (E), (F), (G) and (I). In the histograms, the data are the mean±SEM for seven mice per group. *$p<0.05$, $p<0.01$, *$p<0.005$. #, not detectable.

Unless defined otherwise, all technical and scientific terms used herein have the same meanings as is commonly understood by one of skill in the art to which this invention belongs. If a conflict appears, one should base on this document, including the definitions therein.

As used herein, the articles "a" and "an" refer to one or more than one (i.e., at least one) of the grammatical object of the article. By way of example, "an element" means one element or more than one element.

In the present invention, it is unexpectedly found that citral is effective in improving or alleviating conditions of focal segmental glomerulosclerosis (FSGS), including glomerular epithelial hyperplasia lesions (EPHLs), peri-glomerular inflammation and glomerular hyalinosis or sclerosis, and also reducing proteinuria or hematuria or lowering serum urea nitrogen level or serum creatinine level in FSGS animals. It is found that citral is renoprotective for FSGS which acts via inhibiting the TFG-β fibrosis pathway, reducing oxidative stress through activation of Nrf2 and its downstream genes involved in potent anti-oxidant pathways, reducing inflammation through NF-κB, and decreasing apoptosis by reducing caspase-9, caspase-3, and pro-apoptotic gene Bax. Further, it is found that citral exhibits no apparent adverse side effects to animals and thus has no concern about its safety.

Therefore, the present invention provides a therapeutic approach to treat or ameliorate certain pathological and physiological symptoms of FSGS. Specifically, the method of the invention is effective in reducing one or more symptoms of FSGS including glomerular epithelial hyperplasia lesions (EPHLs), peri-glomerular inflammation or glomerular hyalinosis or sclerosis, in a subject having FSGS. The method of the invention is also effective in reducing proteinuria or hematuria or lowering serum urea nitrogen level or serum creatinine level in a subject with FSGS.

As known in the art, focal segmental glomerulosclerosis (FSGS) is a kidney disease where scaring (sclerosis) occurs in a portion of some (focal) but not all glomeruli, which can be identified by a biopsy of renal tissue. FSGS shows pathological symptoms including glomerular epithelial hyperplasia lesions (EPHLs), a key histopathology index of progression of FSGS, and also peri-glomerular inflammation and glomerular hyalinosis or sclerosis. FSGS also shows renal dysfunction symptoms such as severe proteinuria, hypertension, hypoalbuminemia and hematuria etc. (Cattran D C, Rao P. *American Journal of Kidney Disease*, 21(3):344-9, 1998; Chun M J et al., *Journal of the American Society of Nephrology*, 15:2169, 2004; Rydel J J et al., *American Journal of Kidney Disease*, 25(4):534-42, 1995). As the progression of the disease, the symptoms include thickening of the glomerular basement membrane, increasing of glomerular extracellular matrix, appearance of glass-like deposits in blood vessels, and then formation of scar tissues composed mainly of collagen, accompanied by accumulation of foam cells on the capillary wall, capillary collapse, hyperplasia and hypertrophy of viceral epithelial cells, and podocyte fusion; the sclerotic portion expands gradually with the progression of the disease (D'Agati V D. Curr Opin Nephrol Hypertens 17(3): 271-81, 2008; Hodgin J B et al., American Journal of Clinical Pathology, 177(4):1674-86, 2010; and Thomas D B., The Archives of Pathology and Laboratory Medicine. 133(2):217-23, 2009).

The present invention is based on the unexpected finding that citral is effective in treating focal segmental glomerulosclerosis (FSGS). Patients with FSGS present various symptoms including glomerular epithelial hyperplasia lesions (EPHLs), peri-glomerular inflammation or glomerular hyalinosis or sclerosis, or proteinuria or hematuria, or elevated serum urea nitrogen level or serum creatinine level. The method of the invention is effective in improving any one of these symptoms in patients with FSGS.

As shown in the examples, the FSGS animal models show the features of glomerular epithelial hyperplasia lesions (EPHLs), a key histopathology index of progression of FSGS, peri-glomerular inflammation and progressive glomerular hyalinosis/sclerosis; surprisingly, after treatment with citral for 28 consecutive days at a daily dose of 200 mg/kg of body weight by gavage, the animals show greatly reduced EPHLs, glomerular hyalinosis/sclerosis and peri-glomerular mononuclear leukocyte infiltration, and also reduced proteinuria and lowered serum urea nitrogen level or serum creatinine level.

The citral used in the present invention is an unsaturated chain aldehyde monoterpene containing two double bonds, with the chemical name of 3,7-dimethyl-2,6-octadienal and the molecular formula of $C_{10}H_{16}O$. It appears as a colorless or pale yellow liquid with a heavy lemon scent. There exist two isomers of the following structures:

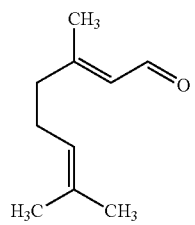

Citral A (E isomer, also known as geranial)

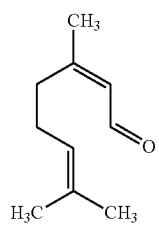

Citral B (Z isomer, also known as neral)

Citral may be obtained commercially or through extraction from natural plant products, including but not limited to lemon oil, citrus oil, *Litsea cubeba* oil, and *Verbena officinalis* oil. It may be extracted from essential oils of natural plants by methods well known in the art, such as distillation and organic solvent extraction, or may be chemically synthesized, for example, using methyl heptenone as starting material. When citral is described as isolated or purified in the present invention, it should be understood as not absolutely isolated or purified, but relatively isolated or purified. For example, purified citral refers to one that is more purified compared to its naturally existing form. In one embodiment, a preparation comprising purified citral may comprise citral in an amount of more than 50%, more than 60%, more than 70%, more than 80%, more than 90%, or 100% (w/w) of the total preparation. It should be understood that when a certain number was used herein to show a ratio or dosage, said number generally includes dosages within the range of 10% more and less, or more specifically, the scope of 5% more and less than the number.

The term "individual" or "subject" used herein includes human and non-human animals such as companion animals (such as dogs, cats and the like), farm animals (such as cows, sheep, pigs, horses and the like), or laboratory animals (such as rats, mice, guinea pigs and the like).

The term "treating" as used herein refers to the application or administration of a composition including one or more active agents to a subject afflicted with a disorder, a symptom of the disorder, or a progression of the disorder, with the purpose to cure, heal, alleviate, relieve, alter, remedy, ameliorate, improve, or affect the disorder, the symptoms of the disorder, the disabilities induced by the disorder, or the progression of the disorder.

The term "therapeutically effective amount" used herein refers to the amount of an active ingredient to confer a therapeutic effect in a treated subject. For example, an effective amount for treating focal segmental glomerulosclerosis is an amount that can prohibit, improve, alleviate or reduce one or more symptoms such as glomerular epithelial hyperplasia lesions (EPHLs), peri-glomerular inflammation or glomerular hyalinosis or sclerosis, or proteinuria or hematuria, or elevated serum urea nitrogen level or serum creatinine level, in a subject having FSGS. The symptoms may be determined and evaluated using methods known in the art based on various disease progress-related indexes, for example by analyzing the amount of urine protein, blood urea nitrogen or serum creatinine, or by analyzing renal sections. The therapeutically effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience. For example, in certain embodiments, the oral dosage of citral used in the present invention is 100 to 1,000 mg/kg daily, specifically 150 to 850 mg/kg daily, more specifically 200 to 700 mg/kg daily, even more specifically 250 to 650 mg/kg daily, further more specifically 300 to 500 mg/kg daily.

According to the present invention, citral may be used as an active ingredient for treating focal segmental glomerulosclerosis. In one embodiment, a therapeutically effective amount of the active ingredient may be formulated with a pharmaceutically acceptable carrier into a pharmaceutical composition of an appropriate form for the purpose of delivery and absorption. Depending on the mode of administration, the pharmaceutical composition of the present invention preferably comprises about 0.1% by weight to about 100% by weight of the active ingredient, wherein the percentage by weight is calculated based on the weight of the whole composition.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. Some examples of appropriate excipients include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered (preferably with a pH value of 3 to 9) as needed. Preparation of an appropriate parenteral composition under sterile conditions may be accomplished with standard pharmacological techniques well known to persons skilled in the art, and no extra creative labor is required.

According to the present invention, citral or compositions comprising citral as the active ingredient may be used in treating individuals with focal segmental glomerulosclerosis. Specifically, citral or compositions comprising citral as the active ingredient may be administered to individuals with focal segmental glomerulosclerosis or individuals with the risk of acquiring focal segmental glomerulosclerosis so as to prevent occurrence of the disease or improve the symptoms or delay deterioration of the symptoms.

In addition, according to the present invention, citral or compositions comprising citral as the active ingredient may be used in combination with existing therapeutic methods or medicaments, such as plasmapheresis or protein adsorption, or pharmaceutical treatment, including but not limited to corticosteroids (such as prednisolone), non-steriodal anti-inflammatory drugs (NSAIDs), cytotoxic drugs (such as cyclophosphamide, chlorambucil, and azathioprine), immunosuppressants (such as cyclosporine and Mycophenolate Mofetil), and vasodilators (such as angiotensin-converting-enzyme inhibitors (ACE inhibitors)). In one embodiment, the medicament or therapeutic method used in combination may be used simultaneously (parallel) or sequentially. When medicaments are used in combination, the medicaments may be mixed in the same formula or put in different formulas separately, such as separate capsules, pills, tablets, and injections.

The present invention is further illustrated by the following examples, which are provided for the purpose of demonstration rather than limitation.

EXAMPLES

In the present study, we used a mouse model of FSGS with the features of glomerular epithelial hyperplasia lesions (EPHLs), a key histopathology index of progression of FSGS, peri-glomerular inflammation, and progressive glomerular hyalinosis/sclerosis. When treated with citral for 28 consecutive days at a daily dose of 200 mg/kg of body weight by gavage, the FSGS mice showed greatly reduced EPHLs, glomerular hyalinosis/sclerosis and peri-glomerular mononuclear leukocyte infiltration, suggesting that Citral may be renoprotective for FSGS and act by inhibiting oxidative stress and apoptosis and early activating the Nrf2 pathway. Meanwhile, a macrophage model involved in anti-oxidative and anti-inflammatory activities was employed and confirmed the beneficial effects of Citral on the FSGS model.

1. Materials and Methods 1.1 Mouse FSGS Model and Experimental Protocol

All animal experiments were performed with the ethical approval of the Institutional Animal Care and Use Committee of The National Defense Medical Center, Taiwan and according to the ethical rules in the NIH *Guide for the Care and Use of Laboratory Animals*. The animals were maintained in the Animal Center of the National Defense Medical Center (Taipei, Taiwan).

A progressive type of mouse FSGS model was used, particularly characterized by EPHLs, a key histopathology index of progression of FSGS, peri-glomerular inflammation, and progressive glomerular hyalinosis/sclerosis [15,39]. The FSGS model was induced in 8-week-old male BALB/c mice (National Laboratory Animal Center, Taipei, Taiwan) by intravenous injection of a single dose of adriamycin (0.10 mg/10 g body weight) (Pfizer, New York, N.Y.) as described previously [15]. Starting three days before adriamycin injection (recorded as day 0 for FSGS model induction), groups of mice (n=7 each) were given a daily dose of Citral (200 mg/kg of body weight) or vehicle (corn oil) by gavage, and were sacrificed on day 7, 14, or 28 after FSGS model induction. Age- and sex-matched BALB/c mice were used as normal controls. Urine samples were collected in metabolic cages on days 3, 7, 14, 21, and 28. Renal cortical tissues and blood samples were collected when the mice were sacrificed and stored appropriately for further analysis. The concentration of urine protein was determined using BCA kits (Pierce, Rockford, Ill.) as described previously [41] and normalized to urine creatinine (Cr) levels measured using kits (Wako Pure Chemical Industries, Osaka, Japan), as described previously [15]. Serum levels of blood urea nitrogen (BUN) and Cr were determined using BUN kits and Cr kits (both from Fuji Dry-Chem Slide, Fuji Film Medical, Tokyo, Japan), as described previously [42].

1.2 Preparation of citral (3,7-dimethyl-2-7-octadienal)

Fruits of *Litsea cubeba*, a traditional Chinese herbal medicine, were obtained from the Lienhuachih Research Center of the Taiwan Forestry Research Institute, Taiwan, in central Taiwan. One kg of the fruits of *Litsea cubeba* was placed in a round-bottom flask to which 3 liter of distilled water was added and the mixture refluxed for 8 h. The essential oil layer above the water was separated, dried with anhydrous sodium sulfate, and placed in specimen bottles. Five grams of fresh oil was dissolved in 5 ml of a 1:8 mixture of ether/n-hexane and purified by HPLC on a Phenomenex Luna Silica [2] column (25 cm long, 1 cm i.d., 5.0 µm) using a Smartline RI Detector 2400 and a Knauer 1000 pump (both from Knauer, Berlin, Germany). The separation conditions were as follows: 1 ml was injected for each separation, the flow rate was 4 ml/min, and the mobile phase was a 1:8 mixture of ether/n-hexane. Citral, 3,7-dimethyl-2-7-octadienal, was eluted with a retention time of 6.08 min. Its structure was confirmed by comparison of the physical and spectral data (including optical rotation EI-MS, $^{13}$C-NMR, and $^1$H-NMR) with previously reported values [40]. Nuclear magnetic resonance spectra were recorded on a Bruker Avance 400 MHz FT-NMR spectrometer. Mass spectra were obtained using a Finnigan MAT-95S mass spectrometer.

1.3 Analysis of Urine Protein and Renal Function

Urine and blood samples were collected from the mice at different time points, which were analyzed for proteinuria and blood urea nitrogen (BUN) and creatinine (Cr) levels by using a urease assay and a picric acid method respectively (*Nephron* 1998; 78: 440-452).

1.4 Pathologic Evaluation

Renal tissues were formalin-fixed, embedded in paraffin, and sections (4 μm) prepared and stained with hematoxylin and eosin (H&E) for renal histopathology as described previously [15] or TUNEL stained for apoptosis as described previously [43]. Renal pathology was examined and renal lesions scored as described previously [39]. For EPHLs and sclerosis, at least 50 glomeruli in sections were examined for each mouse. To detect apoptosis in renal tissues, TUNEL staining was performed using an in situ apoptosis detection kit (Chemicon, Temecula, Calif.) according to the manufacturer's instructions. For immunohistochemistry, methyl Carnoy solution-fixed and paraffin-embedded renal sections were prepared and incubated with goat antibodies against mouse collagen IV (Col-IV) (Southern Biotech, AL) or rabbit antibodies against phosphorylated mouse NF-κB p65 (Cell Signaling Technology, MA), F4/80 (Serotec, Raleigh, N.C.), or CD3 (Serotec), then with horseradish-conjugated rabbit anti-goat IgG antibodies or swine anti-rabbit IgG antibodies (both from Dako, Carpinteria, Calif.). Quantitative image analysis software (Pax-it; Paxcam, VIIIa Park, Ill.) was used to score Col-IV staining and the number of phosphorylated NF-κB p65-, CD3-, F4/80-, or TUNEL-positive cells as described previously [42].

1.5 Measurement of Superoxide Anion and NO

Superoxide anion levels in serum, urine, and kidney tissues were determined as described previously. The results were expressed as relative luminescence units (RLU) per 15 min per milliliter (i.e., RLU/15 min/ml) for serum and urine samples or per milligram dry weight (i.e., RLU/15 min/mg dry weight) for kidney tissues. In addition, renal superoxide anion levels were measured by dihydroethidium (DHE) binding, fluorescence being quantified by counting the percentage of the total nuclei that were positive per kidney cross section as described previously. NO levels in serum and urine were measured using NO detection kits (Abcam, Cambridge, Mass.) according to the manufacturer's instructions.

1.5 Measurement of Renal Nrf2, NAD(P)H Subunit p47$^{phox}$ (p47$^{phox}$), NQO1, HO-1, caspase-3, caspase-8, caspase-9, Bcl-2, and Bax Cytoplasmic and nuclear proteins from renal tissues were prepared using a kit (Active Motif, Tokyo, Japan) according to the manufacturer's instructions and target proteins detected by immunoblotting using goat antibodies against mouse Nrf2 or p47$^{phox}$, (Santa Cruz Biotechnology, Santa Cruz, Calif.) or rabbit antibodies against mouse NQO1 (Abcam), caspase-3, caspase-8, or caspase-9 (all from Cell Signaling Technology, MA) or Bcl2 or Bax (both from Santa Cruz Biotechnology), then with horseradish-conjugated rabbit anti-goat IgG antibodies or goat-anti-rabbit IgG antibodies (both from Santa Cruz Biotechnology) as described previously. Anti-β-actin antibody (Santa Cruz Biotechnology) was used as internal controls for the nuclear and cytosolic target proteins, respectively. Renal HO-1 levels were measured using a commercial ELISA kit (R&D Systems, Minneapolis, Minn.) according to the manufacturer's instructions.

1.6 In Vitro Experiments with Macrophages

RAW-Blue™ cells (Murine macrophages RAW264.7 stably transfected with the NF-κB reporter gene) purchased from InvivoGen (San Diego, Calif.). LPS (from *Escherichia coli* 0111:B4) and mouse antibodies against phospho-ERK1/2, phospho-JNK1/2, and phospho-p38 (all from Sigma, St. Louis, Mo.). Rabbit antibodies against mouse ERK1, JNK1, and p38, and HRP-labeled second antibodies were purchased from Santa Cruz Biotechnology, and IL-1β, IL-6, and TNF-α ELISA kits from R&D Systems. ROS production assay, NO production assay, NF-κB reporter assay, ELISA, and Western blotting were performed as described previously.

1.7 Statistical Analysis

The results for animal model are presented as the mean±SEM. Comparison between two groups was performed using Student's t test. For in vitro experiments, all values are given as mean±SD. Data analysis involved one-way ANOVA with a subsequent Scheffe' test. A value of $p<0.05$ was considered statistically significant.

2. Results

2.1 Citral Ameliorated Mouse FSGS Model

2.1.1 Proteinuria, Renal Function, and Renal Pathology

As shown in FIG. 1A, compared to normal control mice, disease-control FSGS mice treated with vehicle (FSGS+vehicle mice) showed significantly increased proteinuria compared to normal control mice at day 7 after disease induction up to day 28 when the mice were sacrificed. However, in FSGS+Citral mice, this effect was slightly inhibited at day 14 and markedly inhibited at days 21 ($p<0.005$) and 28 ($p<0.01$) compared to FSGS+vehicle mice. In renal function assessment, significantly higher serum levels of BUN (FIG. 1B) and Cr (FIG. 1C) were seen in FSGS+vehicle mice at days 14 (both $p<0.05$) and 28 (both $p<0.005$) than in normal control mice and these effects were almost, or completely, suppressed in FSGS+Citral mice (all $p<0.05$) (FIGS. 1B and 1C). Light microscopy showed that characteristic glomerular EPHLs, suggestive of progression of FSGS lesions, glomerular hyalinosis/sclerosis and peri-glomerular inflammation were both seen at days 14 and 28 in FSGS+vehicle mice, but these renal lesions were greatly decreased in FSGS+Citral mice (all $p<0.01$) (FIG. 1D). Furthermore, FSGS+vehicle mice showed strong renal Col-IV expression at days 14 and 28 and this was markedly inhibited in FSGS+Citral mice (all $p<0.01$) (FIG. 1H). The corresponding quantitative results are shown in FIGS. 1E, F, G and I.

2.1.2 Oxidative Stress in Renal Tissue, Serum, or Urine

ROS and NO

Figure 2:
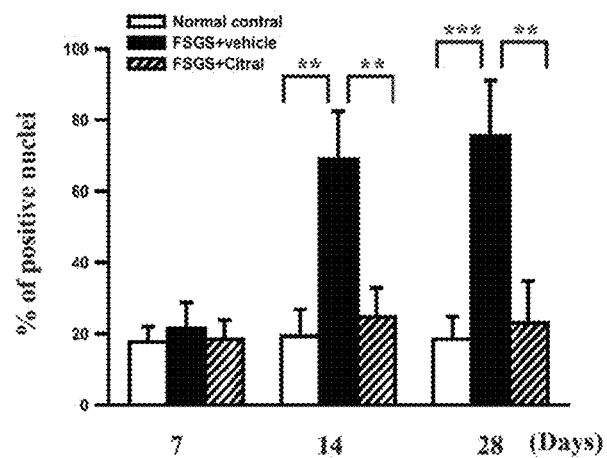
FIG. 2 shows reactive oxygen species (ROS) and nitric oxide (NO) levels in renal tissue (A), serum (B), and urine (C). (D) Kidney in situ ROS production demonstrated by dihydroethidium (DHE) labeling. The arrows indicate positive staining cells. Original magnification, 400×. The scoring is shown in (E). (F, G) NO levels in serum (E) and urine (F). In the histograms, the data are the mean±SEM for seven mice per group. *$p<0.05$, $p<0.01$, *$p<0.005$.
Figure 2:
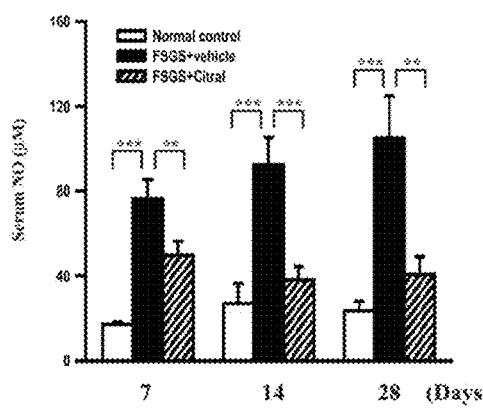
Figure 2:
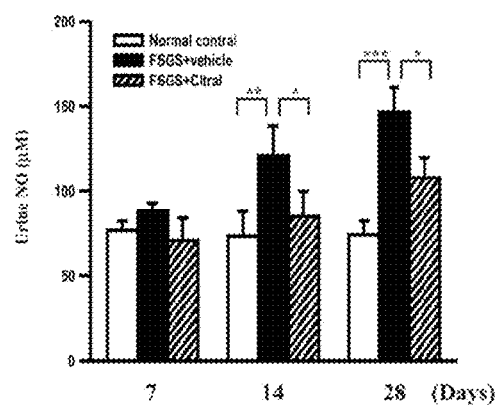

As shown in FIG. 2A-C, compared to normal control mice, FSGS+vehicle mice had significantly higher levels of superoxide anion in renal tissues, serum, and urine (all $p<0.01$) at days 14 and 28 and levels were markedly decreased in FSGS+Citral mice compared to FSGS+vehicle mice (all $p<0.01$). When ROS levels in renal tissues were examined by detection of DHE levels, FSGS mice showed significantly increased renal DHE levels compared to normal control mice at days 14 and 28 (both $p<0.01$) and this effect was suppressed in FSGS+Citral mice (both $p<0.01$) (FIG. 2D). The corresponding quantitative results are shown in FIG. 2E. In addition, FSGS+vehicle mice showed significantly increased NO levels in serum (FIG. 2F) and urine (FIG. 2G) compared to normal control mice at days 14 (both $p<0.01$) and 28 (both $p<0.005$) and levels were significantly reduced in FSGS+Citral mice compared to FSGS+vehicle at days 14 and 28 (all $p<0.05$).

Expression of p47$^{phox}$, Nrf2, NQO1, and HO-1

Since the antioxidant signaling pathway can be activated by reduced production of NAD(P)H oxidase or by activation of Nrf2, we measured protein levels of p47$^{phox}$, nuclear Nrf2 (activation), and HO-1 in the kidney to evaluate the effects of Citral on this pathway. As shown in FIGS. 3A and 3B, p47$^{phox}$ protein levels were significantly increased in FSGS+vehicle at day 28 ($p<0.01$) and this effect was inhibited by Citral administration ($p<0.01$). As shown in FIGS. 3A and 3C, the nuclear Nrf2 expression was significantly decreased in FSGS+vehicle at days 14 and 28 (both $p<0.05$) compared to normal control mice. This effect was inhibited at day 14 in FSGS+Citral mice, although not statistically significant, and obviously, the FSGS+Citral mice showed a greatly increased nuclear Nrf2 levels at day 28 compared to FSGS+vehicle ($p<0.005$) and those of normal control mice ($p<0.05$). In addition, cytosolic levels of NQO1 (FIGS. 3A and 3D) in FSGS+vehicle mice was significantly decreased at days 14 and 28 compared to those of normal control mice (both $p<0.05$), whereas levels in Citral-treated mice were greatly restored to much closer to (day 14) or significantly higher (day 28) ($p<0.01$) than those observed in normal control mice. Moreover, compared to FSGS+vehicle mice with greatly reduced cytosolic levels of HO-1 at days 14 ($p<0.05$) and 28 ($p<0.01$), respectively, compared to normal control mice (FIG. 3E), FSGS+Citral mice showed a significantly elevated HO-1 levels at the both points ($p<0.05$ or $p<0.01$).

2.1.3 Apoptosis, caspases, Bax/Bcl-2 Ratio in Renal Tissue

Figure 4:
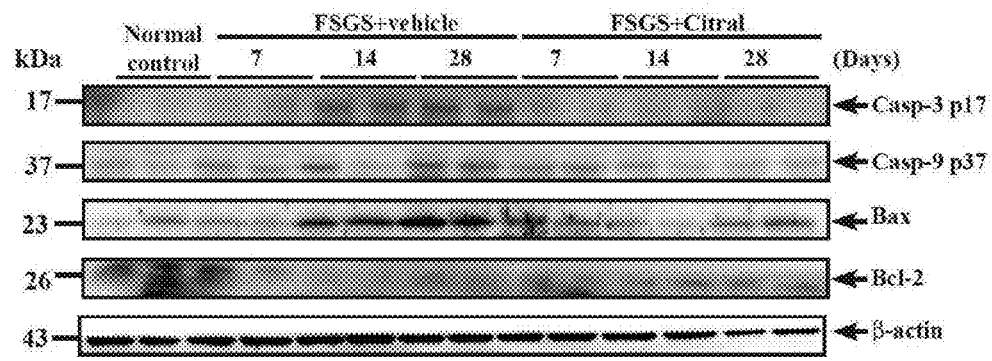
FIG. 4 shows renal apoptosis in the glomerulus and tubule. (A) TUNEL staining in renal tissues at day 7, 14, and 28. Original magnification, 400×. The arrows indicate positively stained cells. The scoring is shown in (B) and (C). (D) Representative Western blot for the active forms of caspase-3 and caspase-9 and Bax and Bcl-2, with β-actin as the internal control. (E-G) Active caspase-3/β-actin ratio (E), active caspase-9/β-actin ratio (F), and Bax/Bcl-2 ratio (G). In the histograms, the data are the mean±SEM for seven mice per group. $*p<0.05$, $p<0.01$, $*p<0.005$.
Figure 4:
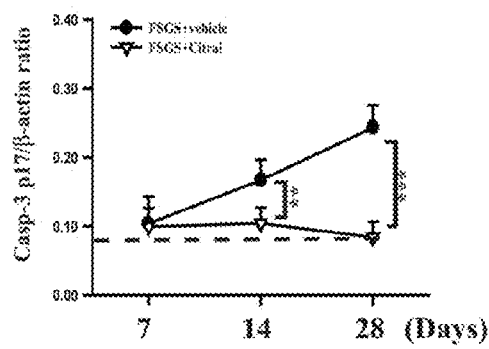
Figure 4:
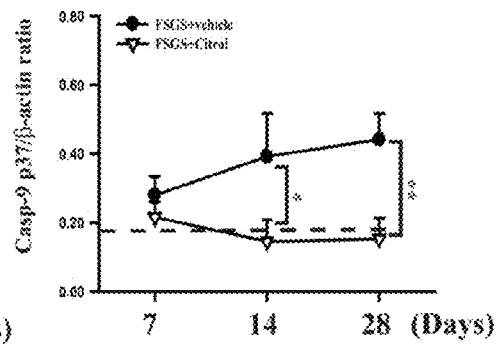
Figure 4:
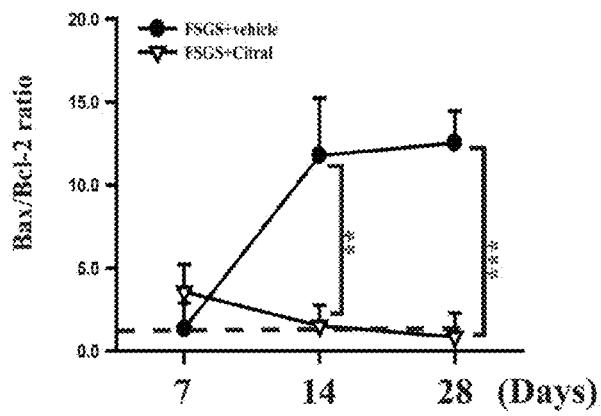

As shown by TUNEL staining (FIG. 4A), although the FSGS+vehicle mice showed markedly increased renal apoptosis levels in the glomerulus and tubular epithelial cells at days 14 and 28 compared to normal control mice (both $p<0.005$), this effect was significantly inhibited in FSGS+Citral mice at day 28 in the glomerulus ($p<0.005$) and both points in the renal tubule. The corresponding quantitative results are shown in FIGS. 4B & 4C. When renal levels of activated caspase-3, caspase-8, and caspase-9 were measured, levels of the mature form (p17 fragment) of caspase-3 were greatly increased in FSGS+vehicle mice compared to normal control mice on days 14 and 28 (both $p<0.01$) and this effect was significantly inhibited in FSGS+Citral mice at days 14 and 28 (both $p<0.01$) (FIGS. 4D and 4E). In addition, as shown in FIGS. 4D and 4F, levels of the mature form (p37 fragment) of caspase-9 were greatly increased in FSGS+vehicle mice ($p<0.01$) and this effect was suppressed in FSGS+Citral mice at days 14 and 28 (both $p<0.05$). There was no detectable difference in levels of the mature form (p18 fragment) of renal caspase-8 between FSGS+vehicle mice, FSGS+Citral mice, and normal control mice (data not shown). Since an increased Bax/Bcl-2 ratio is associated with caspase-9 and caspase-3 activation, we then measured renal levels of Bax and Bcl-2 and found that the Bax/Bcl-2 ratio was increased in FSGS+vehicle mice compared to normal control mice at days 14 and 28 (both $p<0.01$) and this effect was significantly decreased in FSGS+Citral mice at days 14 and 28 (both $p<0.01$) (FIGS. 4B and 4G). These findings suggest that the reduction in renal apoptosis seen in FSGS+Citral mice is due to suppression of the intrinsic pathway of apoptosis.

2.1.4 NF-κB Activation and MCP-1 Expression in Renal Tissues

Figure 5:
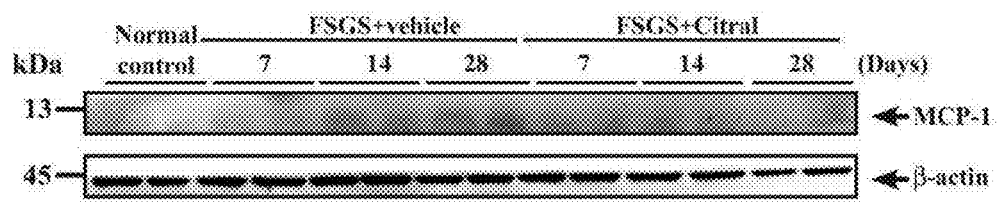
FIG. 5 shows renal NF-κB activation and MCP-1 expression. (A) Detection of NF-κB p65 by immunohistochemical staining. Original magnification, 400×. The arrows indicate positively stained cells. The scoring is shown in (B). (C) Western blot of MCP-1 levels in renal tissues, with β-actin as the internal control for cytosolic protein. (D) MCP-1/β-actin ratio. In the histograms, the data are the mean±SEM for seven mice per group. $*p<0.05$, $***p<0.005$.
Figure 5:
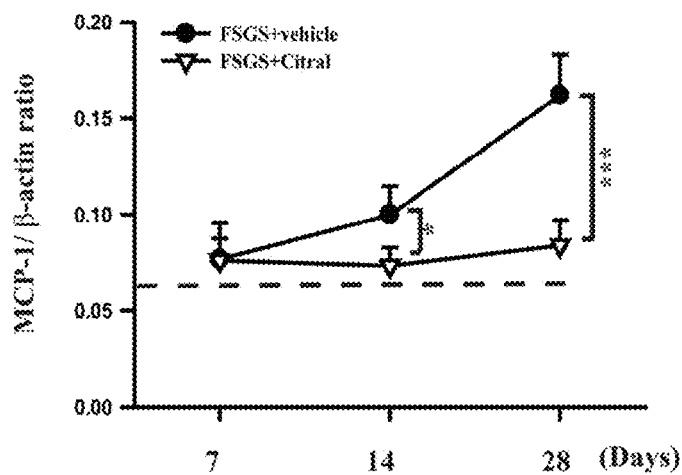

NF-κB activation and the subsequent induction of expression of various proteins, such as MCP-1, are implicated in the development of FSGS. As shown in FIG. 5A, at days 14 and 28 after disease induction, the FSGS+vehicle mice showed significantly increased renal nuclear translocation of phosphorylated NF-κB p65 compared to normal control mice (both $p<0.005$) and this effect was significantly inhibited in the FSGS+Citral mice (both $p<0.005$). The corresponding quantitative results are shown in FIG. 5B. In addition, FSGS+vehicle mice had significantly higher renal MCP-1 levels than normal control mice at days 14 and 28 (both $p<0.05$) and this effect was significantly inhibited in FSGS+Citral mice at days 14 and 28 (both $p<0.05$) (FIGS. 5C and 5D).

2.1.5 Renal Infiltration of T Cells and Macrophages

Figure 6:
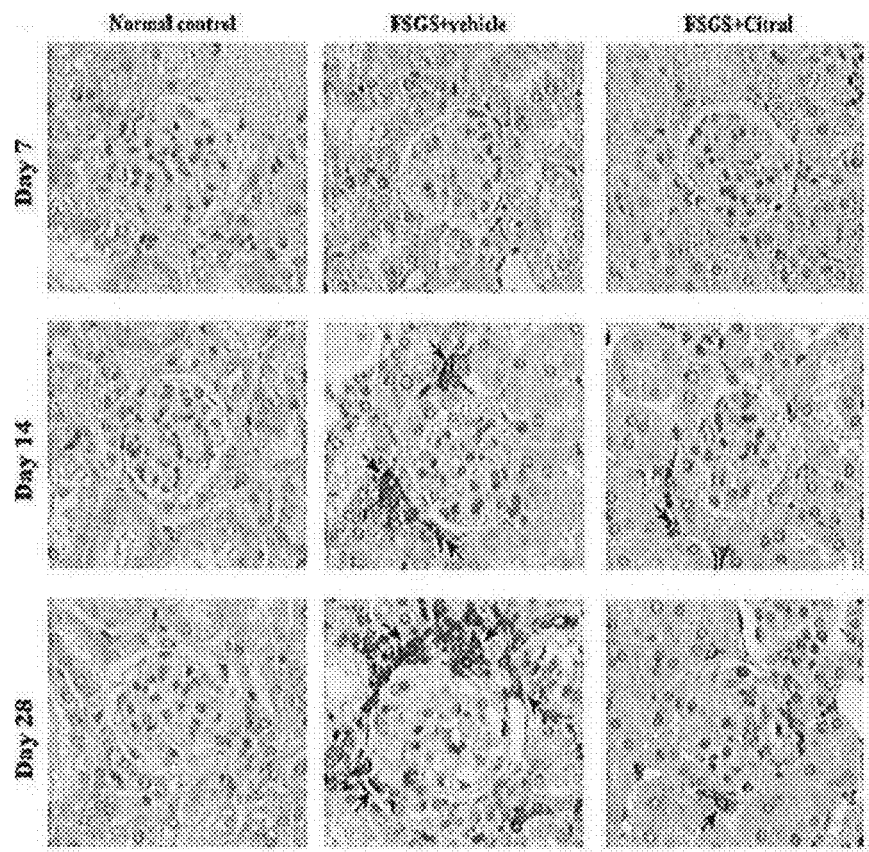
FIG. 6 shows renal T cell and macrophage infiltration. Detection of (A) CD3$^+$ T cells or (C) F4/80$^+$ monocytes/macrophages by immunohistochemical staining. The arrows indicate positively stained cells. Original magnification, 400×. The scoring is shown in (B) and (D). The data are the mean±SEM for seven mice per group. $*p<0.05$, $p<0.01$, $*p<0.005$.
Figure 6:
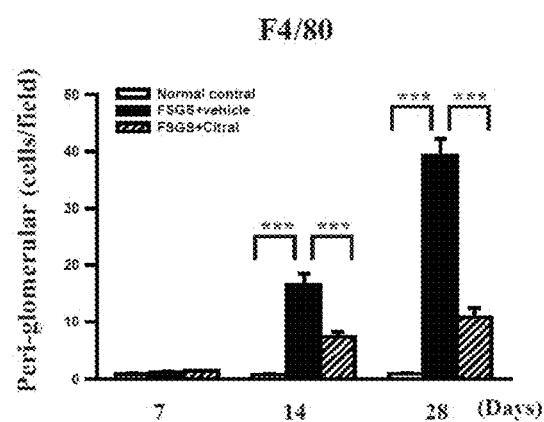

Renal mononuclear leukocyte infiltration is seen in renal tissues of FSGS mice. As shown in FIG. 6A, although significantly increased renal peri-glomerular infiltration of T cells ($CD3^+$) was seen at days 14 and 28 in FSGS+vehicle mice compared to normal control mice (both $p<0.005$), this effect was markedly inhibited in FSGS+Citral mice (both $p<0.05$). The corresponding quantitative results are shown in FIG. 6B. Similarly, as shown in FIG. 6C, FSGS+vehicle mice showing significantly increased peri-glomerular infiltration of macrophages ($F4/80^+$) compared to normal control mice at days 14 and 28 (both $p<0.005$) and this effect was also significantly decreased in FSGS+Citral mice (both $p<0.005$). The corresponding quantitative results are shown in FIG. 6D.

2.2 Citral Inhibited Oxidative Stress and Inflammatory Activities of Macrophages 2.2.1 ROS/NO, NF-κB and Pro-Inflammatory Cytokines The anti-oxidative and anti-inflammatory activities of Citral were examined using LPS-activated RAW 264.7 macrophages. The LPS-induced increase in ROS production was reduced by incubation with Citral (10 μg/ml) or NAC (10 mM), a potent antioxidant, 30 min before and during LPS stimulation (FIG. 7A). The LPS-induced increase in NO generation was inhibited by Citral ($p<0.05$) (FIG. 7B). Further, we examined the effect of Citral on LPS-induced NF-κB activation using NF-κB-dependent alkaline phosphatase reporter cells (RAW-Blue™ cells) and, as shown in FIG. 7C, showing that NF-κB transcriptional activity in LPS-stimulated macrophages was reduced by Citral. Furthermore, in the same system, we showed that the secretion levels of IL-6 (FIG. 7D), TNF-α (FIG. 7E), and IL-1β (FIG. 7F) were inhibited by Citral. These data suggest that Citral was anti-oxidative and anti-inflammatory in the LPS-activated macrophages.

2.2.2 Phosphorylation of ERK1/2, JNK1/2 and p38

LPS can induce macrophage activation and the production of pro-inflammatory cytokines by the activation of various signaling pathways, including the mitogen-activated protein kinase (MAPK) signaling pathways [53]. To examine whether the inhibitory effects of Citral on LPS-induced activation of macrophages are associated with MAPK signaling cascades, RAW 264.7 macrophages were treated with LPS in the presence or absence of Citral (10 μg/ml). The results show that although LPS induced increase in the phosphorylation levels of MAPK, including ERK1/2, JNK1/2 and p38 (FIG. 8A), this effect was significantly inhibited by Citral for ERK1/2 ($p<0.05$) (FIG. 8B) and JNK1/2 ($p<0.05$) (FIG. 8C), except p38 (FIG. 8D). These results suggest that Citral modulated the activation of the MAPK signaling cascades in the LPS-activated macrophages.

3. Discussion

Our study demonstrated that Citral, a purified major active component of *Litsea cubeba*, had renoprotective effects in a FSGS mouse model, including preventing the kidney from glomerular EPHLs, a key histopathology index of progression of FSGS, and from glomerular hyalinosis/sclerosis and mononuclear leukocyte infiltration. These effects were closely associated with reduced oxidative stress, apoptosis and activation of the Nrf2 pathway before the progression of the FSGS model.

Figure 3:
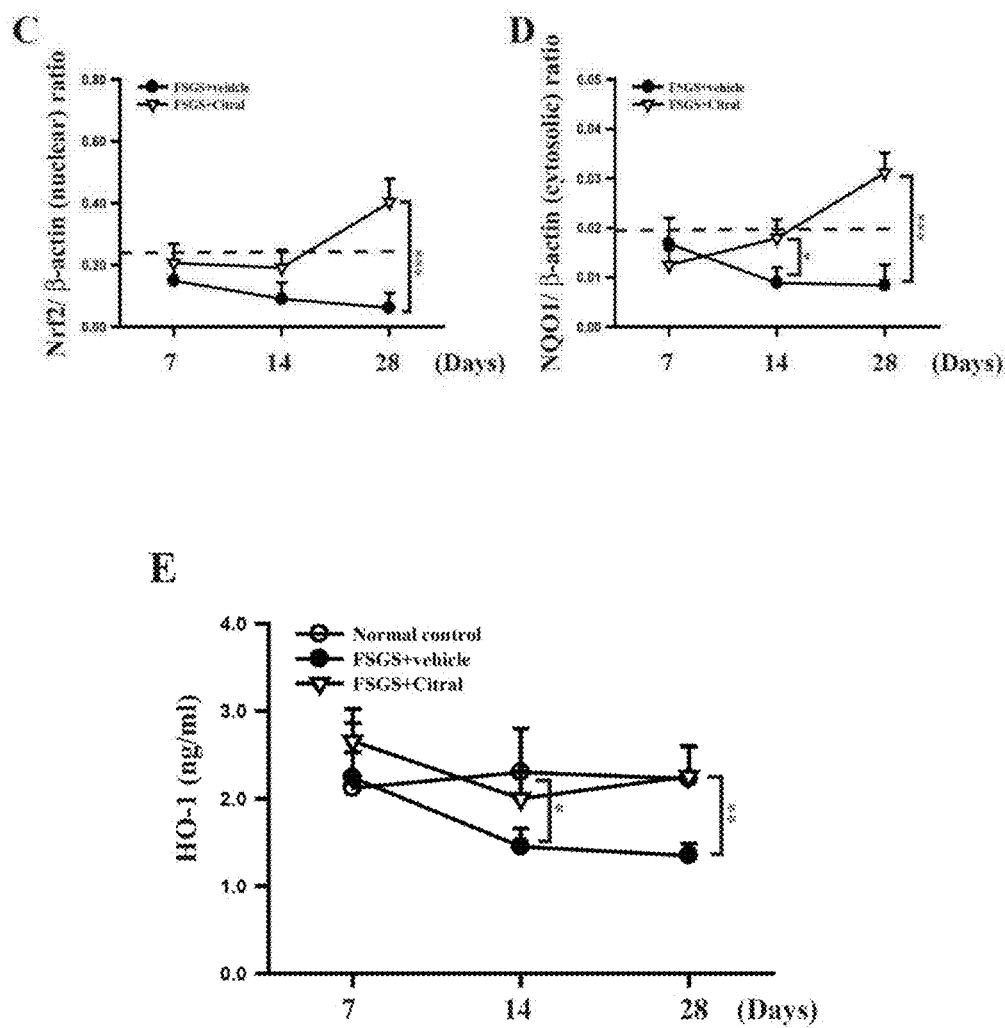
FIG. 3 shows renal nuclear Nrf2 levels, cytosolic p47$^{phox}$, NQO1 and HO-1 levels. (A) Representative Western blot showing levels of cytosolic p47$^{phox}$ and NQO1 and nuclear Nrf2 in kidney tissues. (B-D) Quantification of the p47$^{phox}$/β-actin (cytosolic) ratio (B), the Nrf2/β-actin (nuclear) ratio (C), and the NQO1/β-actin (cytosolic) ratio (D). The horizontal dashed lines indicate levels in normal control mice. (E) HO-1 levels in the kidney. In B-E, the data are the mean±SEM for seven mice per group. $*p<0.05$, $p<0.01$, $*p<0.005$.

First, we showed that Citral administration inhibited the increase in ROS and NO production and $p47^{phox}$ levels seen in FSGS mice and activated the Nrf2 signaling pathway involving increasing expression of its downstream molecules NQO1 and HO-1 during the early developmental stage of this FSGS model, thus contributing to the beneficial effects of Citral on the treated mice (FIG. 3). In this regard, a reduction in nuclear Nrf2 levels is seen in experimental chronic renal failure models [22,54], and impairment of Nrf2 activity is involved in the pathogenesis of oxidative stress- and inflammation-mediated chronic kidney disease [30]. In addition, the NF-κB-mediated inflammatory response is more intense in Nrf2-deficient mice than in wild-type mice [55], and upregulation of Nrf2 suppresses NF-κB activation [56]. Our previous study showed that increased nuclear translocation of Nrf2 is beneficial in the FSGS model [15], confirming previous observations that activation of the Nrf2 signaling pathway is beneficial in experimental chronic renal failure models [22] and in patients with chronic renal insufficiency or failure [28]. Collectively, these findings provide support for a potential therapeutic effect of Citral in renal fibrosis/sclerosis caused by activation of the Nrf2 signaling pathway.

Figure 7:
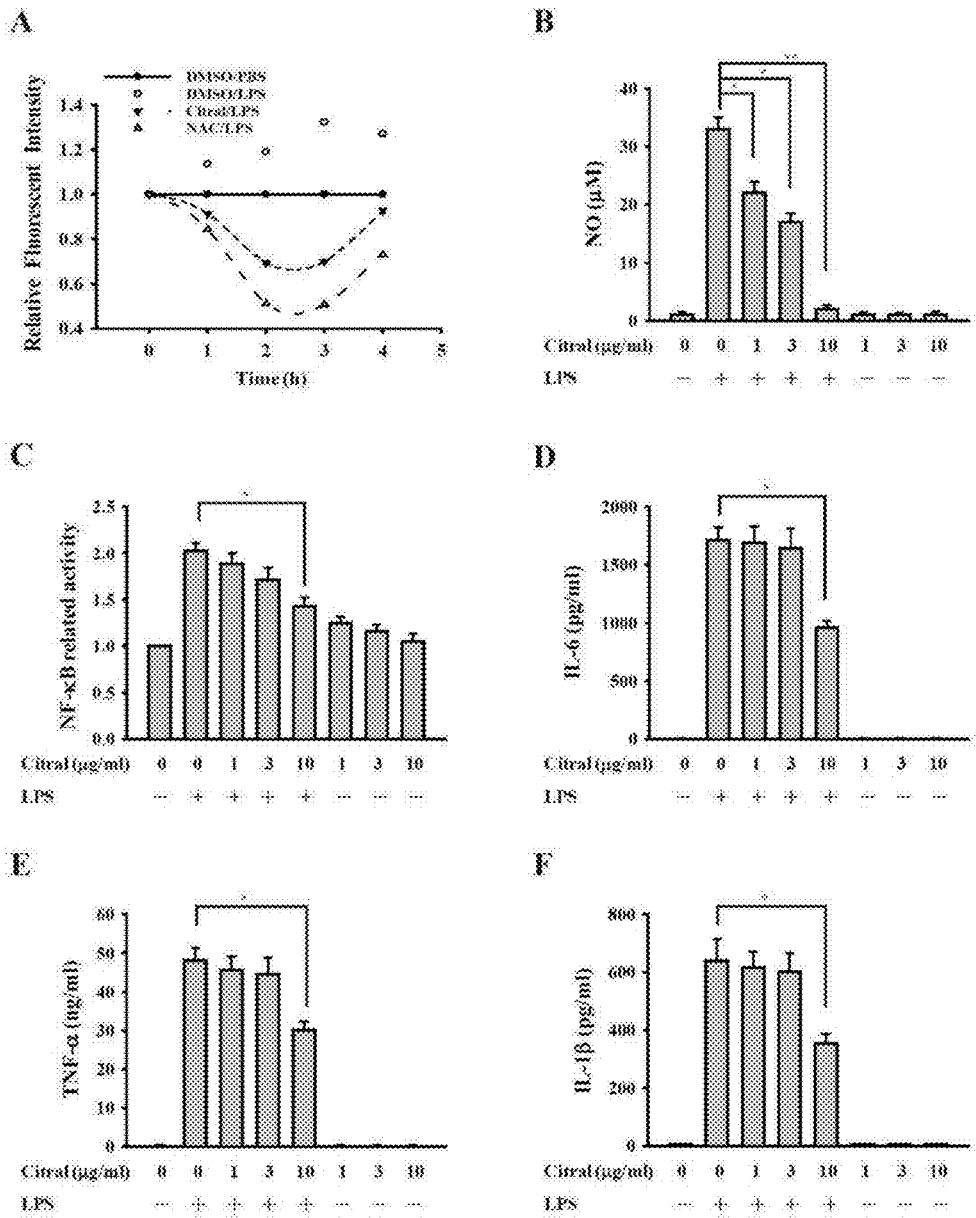
FIG. 7 shows in vitro ROS generation and inflammatory mediator expression. (A) RAW 264.7 macrophages were incubated for 30 min with or without 10 μg/ml Citral or 10 mM N-acetyl cysteine (NAC), then for 0-4 h with or without addition of 1 μg/ml of LPS. ROS production was measured as the relative fluorescence intensity. (B) RAW 264.7 macrophages were incubated for 30 min with or without the indicated concentrations of Citral, then for 24 h with or without addition of 1 μg/ml of LPS, then NO generation in the culture medium was measured by the Griess reaction. (C) RAW-Blue™ cells were incubated for 30 min with or without the indicated concentration of Citral, then for 24 h with or without addition of 1 μg/ml of LPS, then secreted embryonic alkaline phosphatase activity was measured using QUANTI-Blue™. (D-F) RAW 264.7 macrophages were incubated for 30 mM with or without the Citral, then for 24 h with or without addition of 1 μg/ml of LPS, then IL-6 (D), TNF-α (E), and IL-1β(F) in the culture medium were measured by ELISA. The data are expressed as the mean±SD for three separate experiments. $*p<0.05$, $**p<0.01$ compared to the LPS-treated group.
Figure 8:
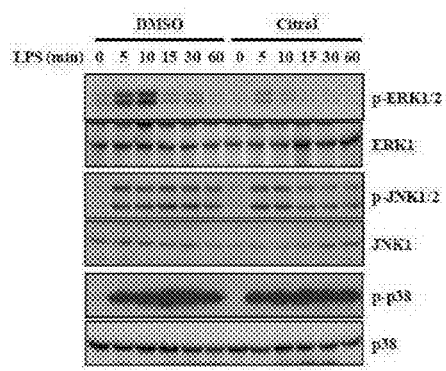
FIG. 8 shows in vitro MAPK phosphorylation. (A) RAW 264.7 macrophages were incubated for 30 min with or without 10 μg/ml Citral, then for 0-60 min with or without addition of 1 μg/ml of LPS, then the phosphorylation levels of ERK1/2, JNK1/2, and p38 were measured by Western blotting. In B-D, the results in the phosphorylation levels of ERK1/2 (B), JNK1/2 (C), and p38 (D) are representative of those obtained in three separate experiments and the histogram shows the results for all three experiments expressed as the mean±SD. $*p<0.05$ compared to the corresponding group without Citral.
Figure 8:
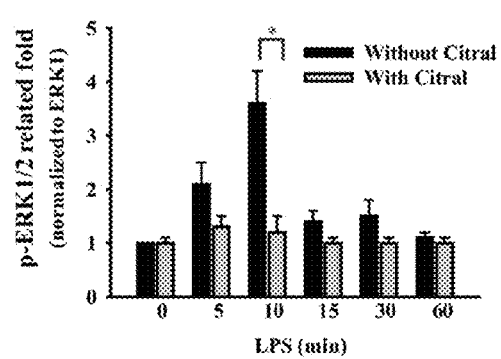
Figure 8:
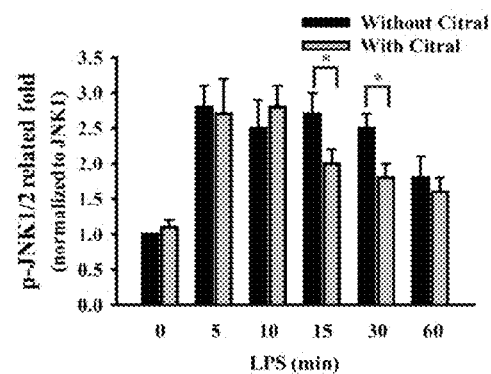
Figure 8:
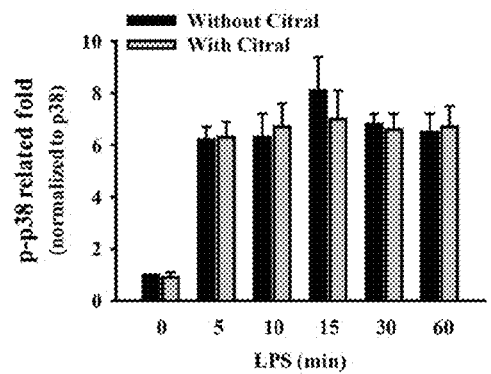

Second, oxidative stress and inflammation are common features of chronic kidney disease [30,57] and play a critical role in the development of renal fibrosis [31,58]. In this regard, our data showed that Citral was anti-oxidative and anti-inflammatory in a model of activated macrophages (FIGS. 7, 8). Oxidative stress and inflammation are closely linked in a vicious cycle, as each amplifies the other [59], and oxidative stress can induce inflammation by activating NF-κB and the subsequent production of proinflammatory cytokines [30,60,61], leading to leukocyte activation and the production and release of ROS/NO [62-64]. In the present study, we demonstrated that Citral administration significantly decreased renal NF-κB activation and MCP-1 expression, resulting in significant inhibition of T cell and macrophage infiltration into the kidney in FSGS+Citral mice, and this effect may contribute to the decrease in glomerular EPHLs which can be promoted by these inflammatory cells [39]. Our data also confirm that EPHLs can be used as a reliable tissue marker for monitoring the progression of FSGS. In our previous study, we found that FSGS mice show increased expression of renal TGF-β1 protein [15], and, in the present study, we demonstrated an increase in levels of its downstream protein Col-IV in the kidney, again supporting the idea that Citral protects the kidney from renal fibrosis in FSGS mice by blocking the TGF-β1-dependent fibrosis pathway (FIG. 1H).

Besides, a number of pathological lesions can arise from oxidative stress-mediated apoptosis [65]. Apoptosis is involved in the development and progression of FSGS [66, 67], and in agreement with this, we showed that inhibition of apoptosis in the kidney by Citral administration was associated with only slight histopathological renal lesions. Furthermore, Citral administration resulted in decreased renal levels of activated caspase-3 and caspase-9 (but not of activated caspase-8) as well as Bax/Bcl-2 ratio (FIG. 4D-G). Nrf2-induced expression of the anti-apoptotic protein Bcl-2 has been shown to enhance cell survival [68,69]. Together, these results suggest that inhibition of apoptosis pathway in the kidney may also contribute to the beneficial effects of treatment on FSGS. However, to our knowledge, there have been no reports of an anti-apoptotic effect of Citral on such an inflammation-associated condition in the kidney, and further investigations are needed.

In summary, our results suggest that Citral may have renoprotective potential for renal inflammation and fibrosis in FSGS, based on its anti-oxidant, anti-apoptotic and anti-inflammatory effects. Further studies on its systemic side effects are warranted before it can be considered for a preclinical validation.

It is generally believed that persons skilled in the art of the present invention should be able to utilize the present invention to its broadest scope based on the descriptions herein without further illustration. Therefore, it should be understood that the descriptions and claims provided herein are for illustration only but do not in any way limit the scope of the present invention.

REFERENCES

1. Cravedi P, Kopp J B, Remuzzi G (2013) Recent Progress in the Pathophysiology and Treatment of FSGS Recurrence. Am J Transplant.
2. D'Agati V D, Alster J M, Jennette J C, Thomas D B, Pullman J, et al. (2012) Association of Histologic Variants in FSGS Clinical Trial with Presenting Features and Outcomes. Clin J Am Soc Nephrol.
3. McCarthy E T, Sharma M, Savin V J (2010) Circulating permeability factors in idiopathic nephrotic syndrome and focal segmental glomerulosclerosis. Clin J Am Soc Nephrol 5: 2115-2121.
4. Abrantes M M, Cardoso L S, Lima E M, Penido Silva J M, Diniz J S, et al. (2006) Predictive factors of chronic kidney disease in primary focal segmental glomerulosclerosis. Pediatr Nephrol 21: 1003-1012.
5. Sozeri B, Mir S, Mutlubas F, Sen S (2010) The long-term results of pediatric patients with primary focal and segmental glomerulosclerosis. Saudi J Kidney Dis Transpl 21: 87-92.
6. Korbet S M (2012) Treatment of primary FSGS in adults. J Am Soc Nephrol 23: 1769-1776.
7. Pani A (2012) Standard immunosuppresive therapy of immune-mediated glomerular diseases. Autoimmun Rev.
8. Braun N, Schmutzler F, Lange C, Perna A, Remuzzi G, et al. (2008) Immunosuppressive treatment for focal segmental glomerulosclerosis in adults. Cochrane Database Syst Rev: CD003233.
9. Korbet S M (2000) The treatment of primary focal segmental glomerulosclerosis. Ren Fail 22: 685-696.
10. Goumenos D S, Tsagalis G, El Nahas A M, Shortland J R, Davlouros P, et al. (2006) Immunosuppressive treatment of idiopathic focal segmental glomerulosclerosis: a five-year follow-up study. Nephron Clin Pract 104: c75-82.
11. Stirling C M (2006) Focal segmental glomerulosclerosis—does treatment work? Nephron Clin Pract 104: c83-84.
12. Passerini P, Scolari F, Frasca G M, Leoni A, Venturelli C, et al. (2009) [Controversial issues in the Giornale Italiano di Nefrologia: how to treat patients with focal segmental glomerular sclerosis]. G Ital Nefrol 26: 563-576.
13. Bruschi M, Candiano G, Della Clana L, Petretto A, Santucci L, et al. (2011) Analysis of the oxido-redox status of plasma proteins. Technology advances for clinical applications. J Chromatogr B Analyt Technol Biomed Life Sci 879: 1338-1344.
14. Musante L, Candiano G, Petretto A, Bruschi M, Dimasi N, et al. (2007) Active focal segmental glomerulosclerosis is associated with massive oxidation of plasma albumin J Am Soc Nephrol 18: 799-810.
15. Tsai P Y, Ka S M, Chao T K, Chang J M, Lin S H, et al. (2011) Antroquinonol reduces oxidative stress by enhancing the Nrf2 signaling pathway and inhibits inflammation and sclerosis in focal segmental glomerulosclerosis mice. Free Radic Biol Med 50: 1503-1516.
16. Benz K, Buttner M, Dittrich K, Campean V, Dotsch J, et al. (2010) Characterisation of renal immune cell infiltrates in children with nephrotic syndrome. Pediatr Nephrol 25: 1291-1298.
17. Munoz M, Rincon J, Pedreanez A, Viera N, Hernandez-Fonseca J P, et al. (2011) Proinflammatory role of angiotensin II in a rat nephrosis model induced by adriamycin. J Renin Angiotensin Aldosterone Syst 12: 404-412.
18. Wang Y, Wang Y P, Tay Y C, Harris D C (2001) Role of CD8(+) cells in the progression of murine adriamycin nephropathy. Kidney Int 59: 941-949.
19. Benchimol C (2003) Focal segmental glomerulosclerosis: pathogenesis and treatment. Curr Opin Pediatr 15: 171-180.
20. Ozbek E (2012) Induction of oxidative stress in kidney. Int J Nephrol 2012: 465897.

21. Rojas-Rivera J, Ortiz A, Egido J (2012) Antioxidants in kidney diseases: the impact of bardoxolone methyl. Int J Nephrol 2012: 321714.
22. Kim H J, Vaziri N D (2010) Contribution of impaired Nrf2-Keap1 pathway to oxidative stress and inflammation in chronic renal failure. Am J Physiol Renal Physiol 298: F662-671.
23. Liu G C, Fang F, Zhou J, Koulajian K, Yang S, et al. (2012) Deletion of p47phox attenuates the progression of diabetic nephropathy and reduces the severity of diabetes in the Akita mouse. Diabetologia 55: 2522-2532.
24. Shen B, Hagiwara M, Yao Y Y, Chao L, Chao J (2008) Salutary effect of kallistatin in salt-induced renal injury, inflammation, and fibrosis via antioxidative stress. Hypertension 51: 1358-1365.
25. Lee J M, Li J, Johnson D A, Stein T D, Kraft A D, et al. (2005) Nrf2, a multi-organ protector? FASEB J 19: 1061-1066.
26. Nguyen T, Nioi P, Pickett CB (2009) The Nrf2-antioxidant response element signaling pathway and its activation by oxidative stress. J Biol Chem 284: 13291-13295.
27. Wilmes A, Crean D, Aydin S, Pfaller W, Jennings P, et al. (2011) Identification and dissection of the Nrf2 mediated oxidative stress pathway in human renal proximal tubule toxicity. Toxicol In Vitro 25: 613-622.
28. Pergola P E, Krauth M, Huff J W, Ferguson D A, Ruiz S, et al. (2011) Effect of bardoxolone methyl on kidney function in patients with T2D and Stage 3b-4 CKD. Am J Nephrol 33: 469-476.
29. Thornalley P J, Rabbani N (2012) Dietary and synthetic activators of the antistress gene response in treatment of renal disease. J Ren Nutr 22: 195-202.
30. Ruiz S, Pergola P E, Zager R A, Vaziri N D (2013) Targeting the transcription factor Nrf2 to ameliorate oxidative stress and inflammation in chronic kidney disease. Kidney Int.
31. Nlandu Khodo S, Dizin E, Sossauer G, Szanto I, Martin P Y, et al. (2012) NADPH-oxidase 4 protects against kidney fibrosis during chronic renal injury. J Am Soc Nephrol 23: 1967-1976.
32. Oh C J, Kim J Y, Choi Y K, Kim H J, Jeong J Y, et al. (2012) Dimethylfumarate attenuates renal fibrosis via NF-E2-related factor 2-mediated inhibition of transforming growth factor-beta/Smad signaling. PLoS One 7: e45870.
33. Cheel J, Theoduloz C, Rodriguez J, Schmeda-Hirschmann G (2005) Free radical scavengers and antioxidants from Lemongrass (Cymbopogon citratus (DC.) Stapf.). J Agric Food Chem 53: 2511-2517.
34. Barroso M F, Noronha J P, Delerue-Matos C, Oliveira MB (2011) Flavored waters: influence of ingredients on antioxidant capacity and terpenoid profile by HS-SPME/GC-MS. J Agric Food Chem 59: 5062-5072.
35. Lee H J, Jeong H S, Kim D J, Noh Y H, Yuk D Y, et al. (2008) Inhibitory effect of citral on NO production by suppression of iNOS expression and NF-kappa B activation in RAW264.7 cells. Arch Pharm Res 31: 342-349.
36. Bachiega T F, Sforcin J M (2011) Lemongrass and citral effect on cytokines production by murine macrophages. J Ethnopharmacol 137: 909-913.
37. Lin C T, Chen C J, Lin T Y, Tung J C, Wang S Y (2008) Anti-inflammation activity of fruit essential oil from *Cinnamomum insularimontanum* Hayata. Bioresour Technol 99: 8783-8787.
38. Ortiz M I, Gonzalez-Garcia M P, Ponce-Monter H A, Castaneda-Hernandez G, Aguilar-Robles P (2010) Synergistic effect of the interaction between naproxen and citral on inflammation in rats. Phytomedicine 18: 74-79.
39. Shui H A, Ka S M, Yang S M, Lin Y F, Lo Y F, et al. (2007) Osteopontin as an injury marker expressing in epithelial hyperplasia lesions helpful in prognosis of focal segmental glomerulosclerosis. Transl Res 150: 216-222.
40. Pouchert C J, Campbell JR (1974) The Aldrich library of NMR spectra: Aldrich Chemical Co.
41. Shui H A, Ka S M, Lin J C, Lee J H, Jin J S, et al. (2006) Fibronectin in blood invokes the development of focal segmental glomerulosclerosis in mouse model. Nephrol Dial Transplant 21: 1794-1802.
42. Ka S M, Yeh Y C, Huang X R, Chao T K, Hung Y J, et al. (2012) Kidney-targeting Smad7 gene transfer inhibits renal TGF-beta/MAD homologue (SMAD) and nuclear factor kappaB (NF-kappaB) signalling pathways, and improves diabetic nephropathy in mice. Diabetologia 55: 509-519.
43. Ka S M, Hsieh T T, Lin S H, Yang S S, Wu C C, et al. (2011) Decoy receptor 3 inhibits renal mononuclear leukocyte infiltration and apoptosis and prevents progression of IgA nephropathy in mice. Am J Physiol Renal Physiol 301: F1218-1230.
44. Tsai P Y, Ka S M, Chang J M, Chen H C, Shui H A, et al. (2011) Epigallocatechin-3-gallate prevents lupus nephritis development in mice via enhancing the Nrf2 antioxidant pathway and inhibiting NLRP3 inflammasome activation. Free Radic Biol Med 51: 744-754.
45. Yang B, Johnson T S, Thomas G L, Watson P F, Wagner B, et al. (2002) A shift in the Bax/Bcl-2 balance may activate caspase-3 and modulate apoptosis in experimental glomerulonephritis. Kidney Int 62: 1301-1313.
46. Liao P C, Chien S C, Ho C L, Wang E I, Lee S C, et al. (2010) Osthole regulates inflammatory mediator expression through modulating NF-kappaB, mitogen-activated protein kinases, protein kinase C, and reactive oxygen species. J Agric Food Chem 58: 10445-10451.
47. Schachter A D, Strehlau J, Zurakowski D, Vasconcellos L, Kim Y S, et al. (2000) Increased nuclear factor-kappaB and angiotensinogen gene expression in posttransplant recurrent focal segmental glomerulosclerosis. Transplantation 70: 1107-1110.
48. Watson D, Zheng G, Wu H, Wang Y M, Wang Y, et al. (2009) CCL2 DNA vaccine to treat renal disease. Int J Biochem Cell Biol 41: 729-732.
49. Wasilewska A, Zoch-Zwierz W, Taranta-Janusz K, Kolodziejczyk Z (2011) Urinary monocyte chemoattractant protein-1 excretion in children with glomerular proteinuria. Scand J Urol Nephrol 45: 52-59.
50. Wang Y, Wang Y, Feng X, Bao S, Yi S, et al. (2001) Depletion of CD4(+) T cells aggravates glomerular and interstitial injury in murine adriamycin nephropathy. Kidney Int 59: 975-984.
51. Wang Y, Wang Y, Cao Q, Zheng G, Lee V W, et al. (2008) By homing to the kidney, activated macrophages potently exacerbate renal injury. Am J Pathol 172: 1491-1499.
52. Wyburn K R, Chadban S J, Kwan T, Alexander S I, Wu H (2013) Interleukin-18 binding protein therapy is protective in adriamycin nephropathy. Am J Physiol Renal Physiol 304: F68-76.
53. Su S C, Hua K F, Lee H, Chao L K, Tan S K, et al. (2006) LTA and LPS mediated activation of protein kinases in the regulation of inflammatory cytokines expression in macrophages. Clin Chim Acta 374: 106-115.
54. Zheng H, Whitman S A, Wu W, Wondrak G T, Wong P K, et al. (2011) Therapeutic potential of Nrf2 activators in streptozotocin-induced diabetic nephropathy. Diabetes 60: 3055-3066.

55. Li W, Khor T O, Xu C, Shen G, Jeong W S, et al. (2008) Activation of Nrf2-antioxidant signaling attenuates NFkappaB-inflammatory response and elicits apoptosis. Biochem Pharmacol 76: 1485-1489.
56. Kim J H, Choi Y K, Lee K S, Cho D H, Baek Y Y, et al. (2012) Functional dissection of Nrf2-dependent phase II genes in vascular inflammation and endotoxic injury using Keap1 siRNA. Free Radic Biol Med 53: 629-640.
57. Pedruzzi L M, Stockler-Pinto M B, Leite M, Jr., Mafra D (2012) Nrf2-keap1 system versus NF-kappaB: the good and the evil in chronic kidney disease? Biochimie 94: 2461-2466.
58. Therrien F J, Agharazii M, Lebel M, Lariviere R (2012) Neutralization of tumor necrosis factor-alpha reduces renal fibrosis and hypertension in rats with renal failure. Am J Nephrol 36: 151-161.
59. Zhang K (2010) Integration of ER stress, oxidative stress and the inflammatory response in health and disease. Int J Clin Exp Med 3: 33-40.
60. Grande M T, Perez-Barriocanal F, Lopez-Novoa J M (2010) Role of inflammation in tubulo-interstitial damage associated to obstructive nephropathy. J Inflamm (Lond) 7: 19.
61. Queisser N, Schupp N (2012) Aldosterone, oxidative stress, and NF-kappaB activation in hypertension-related cardiovascular and renal diseases. Free Radic Biol Med 53: 314-327.
62. Akcay A, Nguyen Q, Edelstein C L (2009) Mediators of inflammation in acute kidney injury. Mediators Inflamm 2009: 137072.
63. Robinson J M (2009) Phagocytic leukocytes and reactive oxygen species. Histochem Cell Biol 131: 465-469.
64. Anders H J, Ryu M (2011) Renal microenvironments and macrophage phenotypes determine progression or resolution of renal inflammation and fibrosis. Kidney Int 80: 915-925.
65. Circu M L, Aw T Y (2010) Reactive oxygen species, cellular redox systems, and apoptosis. Free Radic Biol Med 48: 749-762.
66. Erkan E, Garcia C D, Patterson L T, Mishra J, Mitsnefes M M, et al. (2005) Induction of renal tubular cell apoptosis in focal segmental glomerulosclerosis: roles of proteinuria and Fas-dependent pathways. J Am Soc Nephrol 16: 398-407.
67. Ory V, Fan Q, Hamdaoui N, Zhang S Y, Desvaux D, et al. (2012) c-mip down-regulates NF-kappaB activity and promotes apoptosis in podocytes. Am J Pathol 180: 2284-2292.
68. Niture S K, Jaiswal A K (2012) Nrf2-induced antiapoptotic Bcl-xL protein enhances cell survival and drug resistance. Free Radic Biol Med.
69. Niture S K, Jaiswal A K (2012) Nrf2 protein up-regulates antiapoptotic protein Bcl-2 and prevents cellular apoptosis. J Biol Chem 287: 9873-9886.

What is claimed is:

1. A method for treating focal segmental glomerulosclerosis (FSGS) in a subject in need thereof, which comprises administering a therapeutically effective amount of citral to the subject.
2. The method of claim 1, wherein the method of treating is effective to reduce one or more symptoms of FSGS in the subject selected from the group consisting of glomerular epithelial hyperplasia lesions (EPHLs), peri-glomerular inflammation and glomerular hyalinosis or sclerosis.
3. The method of claim 2, wherein the method of treating is effective to reduce proteinuria or hematuria or lower serum urea nitrogen level or serum creatinine level in the subject.
4. The method of claim 1, wherein the citral is orally administered.
5. The method of claim 1, wherein the citral is administered in combination with one or more therapeutic agent for treating focal segmental glomerulosclerosis selected from the group consisting of orticosteroid drugs, non-steriodal anti-inflammatory drugs (NSAIDs), immunosuppressants, cytotoxic drugs and vasodilators.

\* \* \* \* \*